(12) United States Patent
Mattson et al.

(10) Patent No.: US 8,765,767 B2
(45) Date of Patent: Jul. 1, 2014

(54) POSITIVE ALLOSTERIC MODULATORS OF MGLUR2

(71) Applicant: Bristol-Myers Squibb Company, Princeton, NJ (US)

(72) Inventors: Ronald J. Mattson, Meriden, CT (US); Zhaoxing Meng, Middletown, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/826,760

(22) Filed: Mar. 14, 2013

(65) Prior Publication Data

US 2013/0245042 A1    Sep. 19, 2013

Related U.S. Application Data

(60) Provisional application No. 61/611,973, filed on Mar. 16, 2012.

(51) Int. Cl.
| | |
|---|---|
| C07D 239/42 | (2006.01) |
| C07D 401/04 | (2006.01) |
| A01N 43/42 | (2006.01) |
| A61K 31/44 | (2006.01) |
| C07D 513/02 | (2006.01) |
| C07D 515/02 | (2006.01) |
| C07D 417/00 | (2006.01) |
| C07D 419/00 | (2006.01) |

(52) U.S. Cl.
USPC .......... 514/256; 514/300; 514/303; 546/119; 546/121; 544/333

(58) Field of Classification Search
USPC .................. 514/256, 303, 300; 546/119, 121; 544/333
See application file for complete search history.

(56) References Cited

U.S. PATENT DOCUMENTS

| | | | |
|---|---|---|---|
| 7,297,698 B2 * | 11/2007 | Taniguchi et al. | ....... 514/252.14 |
| 2011/0009441 A1 | 1/2011 | Trabanco-Saurez et al. | |
| 2012/0184525 A1 | 7/2012 | Cid-Nunez et al. | |
| 2012/0184527 A1 | 7/2012 | Cid-Nunez et al. | |
| 2012/0184528 A1 | 7/2012 | Cid-Nunez et al. | |

* cited by examiner

*Primary Examiner* — Niloofar Rahmani
(74) *Attorney, Agent, or Firm* — James Epperson

(57) ABSTRACT

The disclosure generally relates to compounds of formula I, including their salts, as well as compositions and methods of using the compounds. The compounds modulate the mGluR2 receptor and may be useful for the treatment of various disorders of the central nervous system.

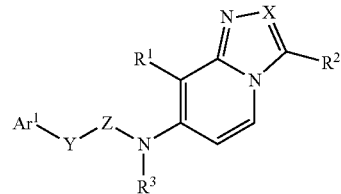

(I)

12 Claims, No Drawings

US 8,765,767 B2

POSITIVE ALLOSTERIC MODULATORS OF MGLUR2

CROSS-REFERENCE TO RELATED APPLICATIONS

This application claims the benefit of U.S. Provisional Application Ser. No. 61/611,973 filed Mar. 16, 2012.

BACKGROUND OF THE INVENTION

The disclosure generally relates to compounds of formula I, including their salts, as well as compositions and methods of using the compounds. The compounds are ligands, agonists and partial agonists for the mGluR2 PAM receptor and may be useful for the treatment of various disorders of the central nervous system.

Glutamate is the major excitatory neurotransmitter in the mammalian brain, playing an important physiological role in a wide variety of processes. Glutamatergic neurotransmission is predominantly mediated through activation of cell surface receptors including ligand-gated ion channels (ionotropic receptors) and metabotropic glutamate G protein coupled receptors (mGluRs). The metabotropic glutamate receptor family is comprised of 8 family members that are part of the family 3 GPCR superfamily. These receptors are further subdivided into Group I (mGluR 1, 5), Group II (mGluR 2, 3) and Group III (mGluR 4, 6, 7, 8) based upon sequence homology, receptor signaling, and pharmacology.

At the cellular level, mGluR2 plays a key role as an autoreceptor in glutamate terminals, though it is generally thought to be localized at the periphery of the synapse, away from the active zone. Activation of the mGluR2 receptor by glutamate or other orthosteric ligands results in a reduction of adenylate cyclase via a Gαi protein and a subsequent reduction of glutamate release from the pre-synaptic terminal. mGluR2 receptors are localized to regions of the brain involved with psychiatric disorders, including the prefrontal cortex, striatum, hippocampus, and amygdala. Excessive glutamate release has been hypothesized to contribute to the underlying pathophysiology in both anxiety and schizophrenia; therefore, activators of mGluR2 receptors may offer therapeutic benefits in these disorders. This biological phenomenon was demonstrated pre-clinically in a study by Moghaddam and Adams (1998) in which they treated rats with phencyclidine (PCP), an NMDA receptor blocker, and detected increased glutamate release in the mPFC and striatum of these animals as well as hyper-locomotion and working memory deficits. The mGluR2/3 agonist, LY-354740, lowered brain glutamate levels and reversed the behavioral effects of PCP. Many more studies have demonstrated efficacy in a variety of pre-clinical models of psychosis and anxiety with mGluR2/3 agonists. Such pre-clinical work led to the development of mGluR2/3 agonists for both anxiety and schizophrenia. Eli Lilly reported therapeutic effects of LY-544344 for anxiety in GAD patients (Dunayevich et al., 2008) and with LY-2140023 for relief of positive and negative symptoms in schizophrenia (Patil et al., 2007).

To date, most of the available pharmacological tools targeting the mGluR2 receptor have been structural analogues of glutamate and act as orthosteric agonists. While demonstrating proof of principle for use in psychiatric disease, agonists have poor pharmacokinetic profiles and poor brain penetration. Furthermore, several pre-clinical studies have demonstrated tolerance to mGluR2/3 agonists upon repeated dosing in rodents (Cartmell et al., 2000; Galici et al., 2005; Jones et al., 2005). Unlike orthosteric agonists, positive allosteric modulators (PAMs) only activate the receptor when glutamate or another orthosteric agonist is present. Therefore, PAMs are thought to retain spatial and temporal activity of glutamate transmission in the brain and would not continuously stimulate the mGluR2 receptor, potentially avoiding tolerance or unwanted side effects of the agonists. Furthermore, since PAMs bind to an allosteric site on the receptor, they can be designed to be selective for the mGluR2 receptor. Pre-clinical studies and early development of mGluR2 PAMs suggest that they will be effective therapies for positive and negative symptoms and co-morbidy anxiety in schizophrenia.

Based on the expression pattern and functional role of mGluR2, this receptor has emerged as an important target for drug discovery in a number of therapeutic indications. In clinical trials, activating mGluR2 was shown to be efficacious in treating anxiety disorders. In addition, activating mGluR2 has been shown to be efficacious in various animal models of schizophrenia, epilepsy, addiction/drug dependence, Parkinson's disease, pain, sleep disorders, and Huntington's disease. See the following publications: Positive allosteric modulators of the metabotropic glutamate receptor 2 for the treatment of schizophrenia. Mark E Fraley; *Expert Opin. Ther. Patents* (2009) 19(8); Biphenyl-indanone A, a positive allosteric modulator of the metabotropic glutamate receptor subtype 2, has antipsychotic- and anxiolytic-like effects in mice. Galici Ruggero; et al. *The Journal of Pharmacology and Experimental Therapeutics* (2006), 318(1), 173-85; Potential psychiatric applications of metabotropic glutamate receptor agonists and antagonists. Krystal, John; et al. *CNS Drugs* (2010), 24(8), 669-693; Postsynaptic and presynaptic group II metabotropic glutamate receptor activation reduces neuronal excitability; in rat midline paraventricular thalamic nucleus. Hermes M L H J; et al.; *The Journal of Pharmacology and Experimental Therapeutics* (2011), 336(3), 840-9; Scaffold hopping from pyridones to imidazo[1,2-a]pyridines. New positive allosteric modulators of metabotropic glutamate 2 receptor. Gary Tresadern, et al.; *Bioorganic & Medicinal Chemistry Letters* 20 (2010) 175-179; 3-Benzyl-1,3-oxazolidin-2-ones as mGluR2 positive allosteric modulators: Hit-to lead and lead optimization. Allen J. Duplantier, et al.; *Bioorganic & Medicinal Chemistry Letters* 19 (2009) 2524-2529. Use of mGluR2 PAMs for the treatment of cocaine dependence: Design and synthesis of an orally active metabotropic glutamate receptor subtype-2 (mGluR2) positive allosteric modulator (PAM) that decreases cocaine self-administration in rats. Dhanya, Raveendra-Panickar; et al.; *Journal of Medicinal Chemistry* (2011), 54(1), 342-353; The mGluR2 Positive Allosteric Modulator BINA Decreases Cocaine Self-Administration and Cue-Induced Cocaine-Seeking and Counteracts Cocaine-Induced Enhancement of Brain Reward Function in Rats. Jin, Xinchun; et al.; *Neuropsychopharmacology* (2010), 35(10), 2021-2036.

The invention provides technical advantages, for example, the compounds are novel and are ligands for the mGluR2 receptor and may be useful for the treatment of various disorders of the central nervous system. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, pharmaceutical compositions, and their use in treating disorders related to levels of tachykinins or serotonin or both.

One aspect of the invention is a compound of formula I

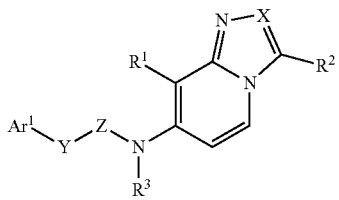

wherein:
R¹ is selected from the group consisting of cyano, halo, alkyl, haloalkyl, (cycloalkyl)alkyl, cycloalkyl, alkoxy, and haloalkoxy;
R² is selected from the group consisting of alkyl, haloalkyl, (cycloalkyl)alkyl, cycloalkyl, OR⁴, and N(R⁵)(R⁶);
R³ is hydrogen or alkyl;
R⁴ is alkyl, haloalkyl, (cycloalkyl)alkyl, or cycloalkyl;
R⁵ is alkyl, haloalkyl, (cycloalkyl)alkyl, or cycloalkyl;
R⁶ is hydrogen or alkyl;
Ar¹ is phenyl or heteroaryl and is substituted with 0-3 substituents selected from cyano, halo, alkyl, haloalkyl, cycloalkyl, alkoxy, and haloalkoxy;
X is CH or N;
Y is $C_{3-6}$ cycloalkyl substituted with 0-2 halo or alkyl substituents; and
Z is a bond or $C_{1-3}$ alkyl;
or a pharmaceutically acceptable salt thereof.

Another aspect of the invention is a compound of formula I where R¹ is selected from the group consisting of cyano, halo, or haloalkyl; R² is selected from the group consisting of alkyl, haloalkyl, (cycloalkyl)alkyl; R³ is hydrogen; Ar¹ is phenyl substituted with 0-3 substituents selected from cyano, halo, alkyl, haloalkyl, cycloalkyl, alkoxy, and haloalkoxy; X is N; Y is $C_{3-6}$ cycloalkyl; and Z is $C_{1-3}$ alkyl; or a pharmaceutically acceptable salt thereof.

Another aspect of the invention is a compound of formula I where R¹ is halo; R² is (cycloalkyl)alkyl; R³ is hydrogen; Ar¹ is phenyl substituted with 0-3 halo substituents; X is N; Y is cyclopropyl; and Z is methylene; or a pharmaceutically acceptable salt thereof.

Another aspect of the invention is a compound of formula I where R¹ is selected from the group consisting of cyano, halo, alkyl, haloalkyl, cycloalkyl, alkoxy, and haloalkoxy.

Another aspect of the invention is a compound of formula I where R² is selected from the group consisting of alkyl, haloalkyl, cycloalkyl, alkoxy, and haloalkoxy.

Another aspect of the invention is a compound of formula I where R³ is hydrogen.

Another aspect of the invention is a compound of formula I where Ar¹ is phenyl substituted with 0-3 substituents selected from cyano, halo, alkyl, haloalkyl, cycloalkyl, alkoxy, and haloalkoxy.

Another aspect of the invention is a compound of formula I where Ar¹ is heteroaryl substituted with 0-3 substituents selected from cyano, halo, alkyl, haloalkyl, cycloalkyl, alkoxy, and haloalkoxy.

Another aspect of the invention is a compound of formula I where X is N.

Another aspect of the invention is a compound of formula I where Y is cyclopropyl.

Another aspect of the invention is a compound of formula I where Z is $C_{1-3}$alkyl.

Another aspect of the invention is a compound of formula I where Z is methylene.

For a compound of formula I, the scope of any instance of a variable substituent, including R¹, R², R³, R⁴, R⁵, R⁶, Ar¹, X, Y, and Z, and can be used independently with the scope of any other instance of a variable substituent. As such, the invention includes combinations of the different aspects.

Unless specified otherwise, these terms have the following meanings. "Halo" includes fluoro, chloro, bromo, and iodo. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some Formula I compounds contain at least one asymmetric carbon atom, an example of which is shown below. The invention includes all stereoisomeric forms of the compounds, both mixtures and separated isomers. Mixtures of stereoisomers can be separated into individual isomers by methods known in the art.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

Compounds of Formula I may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention. The schemes encompass reasonable variations known in the art.

Scheme 1:

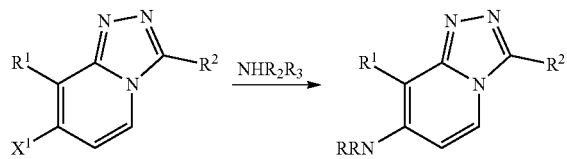

Scheme 2:

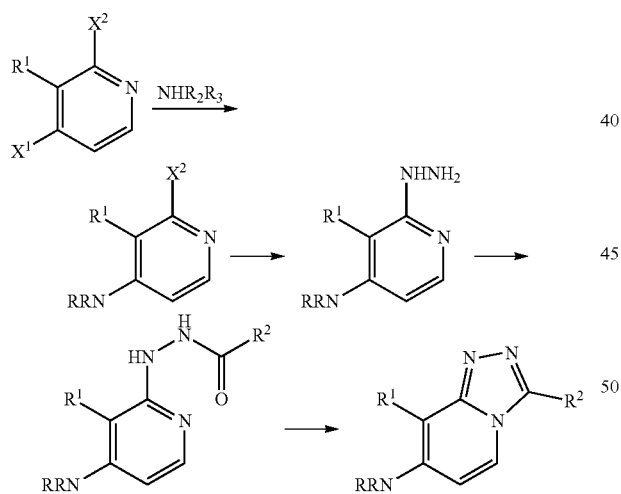

Biological Methods

Cell Culture. Clonally expressed human mGluR2 in HEK293 background was glutamate starved overnight in media without glutamine (GIBCO MEM 12360), containing 10% FBS, 1% penicillin streptomycin.

cAMP Measurement. On the day of the assay, media was removed, cells washed with PBS, cells harvested and pelleted by centrifugation. Cell pellets were resuspended in stimulation buffer without forskolin and counted. A solution of $1.25 \times 10^6$ cells/mL was prepared and dispensed to plates using a Combi liquid handler (Thermo). A standard curve was created using a top concentration of cAMP of 1 μM in the stimulation buffer, 1:3 dilutions over 14 points in the absence of cells. Plates were read by time-resolved fluorescence at 665 nM and 618 nM and a ratio was calculated via in house software, (665 nM/618 nM)*$10^4$. In house software converted the fluorescence value ratios to units of cAMP concentration, which is then used to calculate % inhibition for each test compound.

MGluR2 cAMP Assay Materials and Methods. Compounds were added to white, standard volume 384 non-binding surface plates (Corning 3574). Cells were resuspended in stimulation buffer consisting of Hanks Balanced Salt Solution (14175-095) pH 7.0, 20 mM HEPES, 2.0 mM $CaCl_2$, 5.0 mM $MgCl_2$, and 1 mM IBMX (Sigma 15879), 1 μM forskolin, and 1 μM LY-341495 for 30 min. Buffer without forskolin was used as a negative control. Solutions of D2 and cryptate detection reagents from the CISBIO dynamic cAMP kit (62AM4PEJ) were diluted 1:40 in lysis buffer. Lysis buffer consisted of 50 mM Phosphate Buffer pH 7.0, 800 mM Potassium Fluoride, 0.2% BSA, and 1.0% Triton. Assay reaction was terminated by addition of detection reagents in lysis buffer. One hour later, plates were read on a PE Viewlux. Data was extracted, and concentration response curves generated by fitting the data to a standard 4 parameter logistic equation from which $EC_{50}$ values were determined. See table 1.

TABLE 1

| Example | $EC_{50}$ (nM) |
|---|---|
| 1 | 9 |
| 2 | 26 |
| 3 | 5 |
| 4 | 5 |
| 5 | 5 |
| 6 | 7 |
| 7 | 6 |
| 8 | 12 |
| 9 | 4 |
| 10 | 6 |
| 11 | 12 |
| 12 | 83 |
| 13 | 102 |
| 14 | 55 |
| 15 | 31 |
| 16 | 46 |
| 17 | 6 |
| 18 | 244 |
| 19 | 367 |
| 20 | 2 |
| 21 | 2 |
| 22 | 1 |
| 23 | 1 |
| 24 | 1 |
| 25 | 41 |
| 26 | 54 |
| 27 | 20 |
| 28 | 59 |
| 29 | 81 |
| 30 | 108 |
| 31 | 24 |
| 32 | 44 |
| 33 | 1 |
| 34 | 1 |
| 35 | 3 |
| 36 | 2 |
| 37 | 4 |
| 38 | 4 |
| 39 | 1 |
| 40 | 7 |
| 41 | 2 |
| 42 | 6 |
| 43 | 2 |

TABLE 1-continued

| Example | EC$_{50}$ (nM) |
|---|---|
| 44 | 2 |
| 45 | 12 |
| 46 | 5 |

Pharmaceutical Compositions and Methods of Treatment

Compounds of formula I modulate mGluR2 and can be useful in treating neurological or psychiatric disorders. Therefore, another aspect of the invention is a composition comprising a compound of formula I or a pharmaceutically acceptable salt thereof, and a pharmaceutically acceptable carrier.

Another aspect of the invention is a method for the treatment of anxiety, schizophrenia, epilepsy, addiction/drug dependence, Parkinson's disease, pain, sleep disorders, or Huntington's disease, or other neurological or psychiatric disorders associated with glutamate dysfunction, which comprises administering to a patient a therapeutically affective amount of a compound of formula I.

Another aspect of the invention is a method for the treatment of anxiety or schizophrenia which comprises administering to a patient a therapeutically affective amount of a compound of formula I.

Another aspect of the invention is a method for the treatment of anxiety which comprises administering to a patient a therapeutically affective amount of a compound of formula I.

Another aspect of the invention is a method for the treatment of schizophrenia which comprises administering to a patient a therapeutically affective amount of a compound of formula I.

Another aspect of the invention is the use of a compound of formula I in the manufacture of a medicament for the treatment of neurological or psychiatric disorders.

Another aspect of the invention is the use of a compound of formula I in the manufacture of a medicament for the treatment of anxiety, schizophrenia, epilepsy, addiction/drug dependence, Parkinson's disease, pain, sleep disorders, or Huntington's disease, or other neurological or psychiatric disorders associated with glutamate dysfunction.

Another aspect of the invention is the use of a compound of formula I in the manufacture of a medicament for the treatment of anxiety.

Another aspect of the invention is the use of a compound of formula I in the manufacture of a medicament for the treatment of schizophrenia.

"Patient" means a person suitable for therapy as understood by practitioners in the field of affective disorders and neurodegenerative disorders.

"Treatment," "therapy," and related terms are used as understood by practitioners in the field of neurological and psychiatric disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

DESCRIPTION OF SPECIFIC EMBODIMENTS

The following experimental procedures describe the synthesis of some Formula I compounds. Standard chemistry conventions are used in the text unless otherwise noted. The experimental encompass reasonable variations known in the art. The following HPLC conditions may be used where indicated.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for t-butoxycarbonyl, "DMSO" for dimethylsulfoxide; "h" for hours; "rt" for rt or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for sat'd, "MW" for molecular weight, "mp" for melting point, "ee" for enantiomeric excess, "MS" or "Mass Spec" for mass spectrometry, "ESI" for electrospray ionization mass spectroscopy, "HR"

for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

INTERMEDIATE 1 tert-Butyl (4-chloropyridin-2-yl)carbamate. A 500 mL round bottom flask was charged with 4-chloropyridin-2-amine (9.15 g, 71.2 mmol) which was dissolved in DCE (225 mL). To that stirring solution was added di-tert-butyl dicarbonate (16.31 g, 74.7 mmol) followed by slow addition of DMAP (1.739 g, 14.23 mmol). Vigorous bubbling persisted for about 20 min after which the reaction was analyzed by LCMS which showed clean and complete consumption of the starting material to a large peak with the desired mass (m/z=174 [M-55]) Methanol/Water/TFA Phenomenex Luna C18, 30×2 mm, 3u ES+/−). The contents of the flask were transferred into a separatory funnel and the organic was washed twice with a sat'd sodium bicarbonate, and brine. The aqueous was back extracted with EtOAc and discarded. The combined organics were washed with brine, dried with magnesium sulfate, and concentrated under reduced pressure. The crude solid was diluted with ethanol and the resulting solid was collected by filtration and washed with ethanol. $^1$H NMR of the pale yellow solid was consistent with desired product. The mother liquor was reconcentrated and diluted with a minimal amount of ethanol and placed in the freezer for 10 min. The second crop was collected by filtration and 1H NMR showed it was of equal purity to the first crop. The two crops combined gave tert-butyl (4-chloropyridin-2-yl)carbamate (9 g, 55% yield). $^1$H NMR (400 MHz, CHLOROFORM-d) δ ppm 8.19-8.12 (m, 1H), 8.06 (d, J=1.8 Hz, 1H), 7.93 (br. s., 1H), 6.97 (dd, J=5.4, 1.9 Hz, 1H), 1.54 (s, 9H).

INTERMEDIATE 2 tert-Butyl (4-chloro-3-iodopyridin-2-yl)carbamate. To a 250 mL round bottom flask was charged with tert-butyl (4-chloropyridin-2-yl)carbamate (5 g, 21.87 mmol) and dissolved in THF (109 mL). The stirring solution was placed in a dry ice bath and cooled to −78° C. TMEDA (8.25 mL, 54.7 mmol) was then added and the flask was flushed with nitrogen. 2.5M n-BuLi in hexanes (21.87 mL, 54.7 mmol) was then added over a period of 30 min. The mixture was stirred at −78° C. for 1 h then treated drop wise with a solution of iodine (13.87 g, 54.7 mmol) in anhydrous THF (16 mL) at −78° C. After the addition was complete, the reaction was stirred at −78° C. for 30 min then allowed to warm to rt. The mixture was treated with a solution of sodium hydrogen sulfite (16 g) in H$_2$O (100 mL) and stirred for 30 min then extracted with EtOAc. The extract was washed with brine, dried (MgSO$_4$) and concentrated in vacuo. The product was purified by flash chromatography: (90 g, equilibrated with DCM, loaded with DCM, initial waste: 0 mL, fraction size: 27 mL 18×150 mm, and eluted with MeOH in dichloromethane 0% [180 mL], 0-5% [360 mL], 5% [700 mL]). Collected fractions to give tert-butyl (4-chloro-3-iodopyridin-2-yl)carbamate (6.59 g, 85% yield) as a yellow solid. $^1$H NMR (400 MHz, CHLOROFORM-d) δ ppm 8.28 (d, J=5.0 Hz, 1H), 7.43 (br. s., 1H), 7.10 (d, J=5.0 Hz, 1H), 1.56 (s, 9H)

INTERMEDIATE 3

4-Chloro-3-iodopyridin-2-amine. A 250 mL round bottom flask was charged with tert-butyl (4-chloro-3-iodopyridin-2-yl)carbamate (4.5 g, 12.69 mmol) and dissolved in DCE (50.8 mL). To that stirring solution was added anisole (2.77 mL, 25.4 mmol) followed by TFA (14.67 mL, 190 mmol) at rt. After 1.5 hours, LCMS showed clean and complete consumption of the starting material to a large peak with the desired mass (m/z=254 [M+H]+Methanol/Water/TFA Phenomenex Luna C18, 30×2 mm, 3u ES+/−). The mixture was concentrated under reduced pressure into a collection bulb that was pretreated with 3.0 M NaOH. The crude mixture was then redissolved in toluene to aid in the removal of any volatiles. The crude solid was then diluted with EtOAc and sat'd sodium bicarbonate. The mixture was stirred for 15 min. The contents of the flask were transferred into a separatory funnel where the aqueous layer was extracted twice with EtOAc and discarded. The combined organics were washed with brine, dried with magnesium sulfate, and concentrated under reduced pressure. The crude material was dissolved in a small amount of ethanol and then heated with a heat gun. The mixture was let sit and then after 5 min cooled in an acetone dry ice bath. The solids were sonicated and collected by filtration. The mother liquor was concentrated and the above procedure was repeated. 4-chloro-3-iodopyridin-2-amine (2.1 g, 65% yield) was collected as a solid. $^1$H NMR (400 MHz, CHLOROFORM-d) δ ppm 7.88 (d, J=5.3 Hz, 1H), 6.74 (d, J=5.3 Hz, 1H), 5.20 (br. s., 2H).

INTERMEDIATE 4

2-Bromo-4,4,4-trifluorobutanal. A 200 mL round bottom flask was charged with 4,4,4-trifluorobutanal (5 g, 39.7 mmol) and diluted with diethyl ether (79 mL). The flask was placed in an ice bath and the reaction mixture was cooled to 0° C. Bromine (2.043 mL, 39.7 mmol) was then added drop wise over the course of 15 min. After which the reaction was stirred for 15 min and then let warm to rt. After 3.5 hours, NMR showed complete consumption of the starting material to desired product. The mixture was cooled in an ice bath and slowly quenched with sat'd sodium bicarbonate. The contents of the flask were transferred to a separatory funnel where the layers were separated and the organics were washed with bicarbonate, brine, and dried with magnesium sulfate. A short path distillation apparatus was equipped to the flask and the combination was placed in an oil bath set to 40° C. After 15 min, the flask was removed from the oil bath and the crude residue was distilled at moderate vacuum (~50 torr) to remove any lower boiling point impurities as well as excess diethyl ether. The atmosphere was restored to normal once bubbling had subsided for 5 min. This process was repeated a few times to remove the majority of diethyl ether. $^1$H NMR consistent with desired. 2-bromo-4,4,4-trifluorobutanal (7.4 g, 91% yield). $^1$H NMR (400 MHz, CHLOROFORM-d) δ ppm 9.54-9.36 (m, 1H), 4.52-4.46 (m, 1H), 3.21 (dqd, J=16.0, 10.1, 5.8 Hz, 1H), 2.73-2.62 (m, 1H).

INTERMEDIATE 5

7-Chloro-8-iodo-3-(2,2,2-trifluoroethyl)imidazo[1,2-a]pyridine. A 2.0-5.0 mL microwave vial was charged with 2-bromo-4,4,4-trifluorobutanal (403 mg, 1.965 mmol) dissolved in EtOH (2500 µl). To that stirring solution was added 4-chloro-3-iodopyridin-2-amine (250 mg, 0.982 mmol). The vial was sealed and heated in the microwave for 1 h at 150° C. After 1 hour, LCMS showed clean and complete consumption of the starting material to a single peak with the desired mass (m/z=260 [M+H]+; Methanol/Water/TFA Phenomenex Luna C18, 30×2 mm, 3u ES+/−). The mixture was transferred into a round bottom flask and the ethanol was removed under reduced pressure. The crude mixture was diluted with EtOAc and sat'd sodium bicarbonate. The contents of the flask were transferred into a separatory funnel where the aqueous was extracted twice with EtOAc and discarded. The combined organics were washed with brine, dried with magnesium sulfate, concentrated under reduced pressure, and purified by flash chromatography: (25 g, equilibrated with hexanes, loaded with DCM, initial waste: mL, fraction size: 9 mL 13×100 mm, and eluted with EtOAc in hexanes 0% [115 mL], 10% [150 mL], 20% [400 mL], 30% [400 mL]). Collected fractions to give 7-chloro-8-iodo-3-(2,2,2-trifluoroethyl)imidazo[1,2-a]pyridine (261 mg, 73.7% yield) as a sticky yellow oil. $^1$H NMR (400 MHz, CHLOROFORM-d) δ ppm 7.94 (d, J=7.3 Hz, 1H), 7.70 (s, 1H), 6.98 (d, J=7.3 Hz, 1H), 3.72 (q, J=9.9 Hz, 2H).

INTERMEDIATE 6

7-Chloro-3-(2,2,2-trifluoroethyl)-8-(trifluoromethyl)imidazo[1,2-a]pyridine. A 2.0-5.0 mL microwave vial was charged with 7-chloro-8-iodo-3-(2,2,2-trifluoroethyl)imidazo[1,2-a]pyridine (30 mg, 0.083 mmol) dissolved in DMF (832 μl). To that stirring solution was added dicyanozinc (5.86 mg, 0.050 mmol) followed by tetrakis(triphenylphosphine)palladium(0) (28.8 mg, 0.025 mmol). The vial was sealed and degassed using sonication and ultra pure argon for 1 min. After which the vial was placed into a reaction block preheated to 120° C. After 5 hours, LCMS showed a good proportion of desired product by mass (m/z=260 [M+H]+Methanol/Water/Ammonium Acetate Phenomenex Luna C18, 30×2 mm, 3u ES+/−). The mixture was cooled to rt and diluted with sat'd sodium bicarbonate and EtOAc. The organic was washed with brine, dried with magnesium sulfate, concentrated under reduced pressure, and purified by flash chromatography: (4 g, equilibrated with none, loaded with DCM, initial waste: 0 mL, fraction size: 12 mL 16×100 mm, and eluted with EtOAc in hexanes 0% [20 mL], 0-100% [120 mL]). Collected fractions to give 7-chloro-3-(2,2,2-trifluoroethyl)imidazo[1,2-a]pyridine-8-carbonitrile (18.5 mg, 86% yield) as a plaque white solid. $^1$H NMR (400 MHz, CHLOROFORM-d) δ ppm 8.16 (d, J=7.3 Hz, 1H), 7.78 (s, 1H), 7.06 (d, J=7.3 Hz, 1H), 3.78 (q, J=9.8 Hz, 2H).

INTERMEDIATE 7

7-Chloro-3-(2,2,2-trifluoroethyl)imidazo[1,2-a]pyridine-8-carbonitrile. A 2.0-5.0 mL microwave vial was charged with 7-chloro-8-iodo-3-(2,2,2-trifluoroethyl)imidazo[1,2-a]pyridine (50 mg, 0.139 mmol) and dissolved in DMF (1387 μl). To that stirring solution was added sodium cyanide (7.14 mg, 0.146 mmol) followed by copper(I) iodide (39.6 mg, 0.208 mmol). The vial was sealed and degassed using ultra pure argon and sonication for 2 min. The vial was then placed in a reaction block preheated to 120° C. After 2 hours, LCMS showed ~7.5:1 (product:starting material). The mixture was diluted with EtOAc and sat'd sodium bicarbonate and the contents of the flask were transferred into a separatory funnel where the aqueous was extracted twice with EtOAc and discarded. The combined organics were washed with brine, dried with magnesium sulfate, and concentrated under reduced pressure. The crude was taken on into a coupling reaction without any further purification. $^1$H NMR (400 MHz, DMSO-d$_6$) δ ppm 8.95 (d, J=7.3 Hz, 1H), 7.78 (s, 1H), 7.43 (d, J=7.5 Hz, 1H), 4.30 (q, J=11.0 Hz, 2H).

INTERMEDIATE 8

(E)-3-(4-fluorophenyl)-N-methoxy-N-methylacrylamide. A suspension of (E)-3-(4-fluorophenyl)acrylic acid (6 g, 36.1 mmol) and thionyl chloride (20.0 mL, 274 mmol) in dichloromethane (10 mL) and DMF (1 drop) was heated to reflux for 2 h to give a clear solution. The solution was concentrated. A solution of the residue in dichloromethane (100 mL) was added to a solution of N,O-dimethylhydroxylamine, HCl (4.23 g, 43.3 mmol) and pyridine (11.68 mL, 144 mmol) in dichloromethane (200 mL) with ice bath cooling. The cooling bath was removed and the pale yellow suspension was stirred at rt for 16 hr. The mixture was diluted with dichloromethane, washed with H$_2$O, washed with 1N HCl, dried over magnesium sulfate, and concentrated to give (E)-3-(4-fluorophenyl)-N-methoxy-N-methylacrylamide as a light yellow oil (7.1 g, 94%) that solidified upon standing to large crystals. $^1$H NMR (400 MHz, CHLOROFORM-d) δ 7.72 (d, J=15.8 Hz, 1H), 7.63-7.54 (m, 2H), 7.14-7.05 (m, 2H), 6.98 (d, J=15.8 Hz, 1H), 3.79 (s, 3H), 3.34 (s, 3H). LCMS: M+1=210.15

INTERMEDIATE 9

Trans-2-(4-fluorophenyl)-N-methoxy-N-methylcyclopropanecarboxamide. In a 1 L three neck flask, DMSO (100 mL) was rapidly stirred as 60% sodium hydride in mineral oil (4.59 g, 115 mmol) was added in 1.5 g portions. After the foaming subsided, trimethylsulfoxonium iodide (25.2 g, 115 mmol) was added portion wise over a 1 h period, maintaining the temperature below 35° C. The reaction was stirred at rt for 30 min. A soln of (E)-3-(4-fluorophenyl)-N-methoxy-N-methyl acrylamide (8 g, 38.2 mmol) in DMSO (50 mL) was then added dropwise maintaining the temperature below 35° C. After 45 min, the reaction was then slowly quenched with sat'd ammonium chloride (25 mL). The solution was then diluted with EtOAc. The solution was washed with water, dried with brine, dried over magnesium sulfate, and concentrated to give trans-2-(4-fluorophenyl)-N-methoxy-N-methylcyclopropanecarboxamide as a clear oil (8.1 g, 95%). $^1$H NMR (400 MHz, CHLOROFORM-d) δ 7.16-7.08 (m, 2H), 7.05-6.93 (m, 2H), 3.72 (s, 3H), 3.26 (s, 3H), 2.55-2.45 (m, 1H), 1.64 (ddd, J=9.2, 5.1, 4.3 Hz, 1H), 1.34-1.29 (m, 2H). LCMS: M+1=224.16.

INTERMEDIATE 10

Chiral resolution of racemic trans-2-(4-fluorophenyl)-N-methoxy-N-methylcyclopropane Carboxamide. A solution of trans-2-(4-fluorophenyl)-N-methoxy-N-methylcyclopropanecarboxamide (1.1 g, 4.93 mmol) in a 50% soln of ethanol/heptane was resolved by Chiral Prep HPLC on a ChiralPak-AD column, 5 cm×50 cm, using 10% ethanol/pentane containing 0.1% diethyl amine as the eluent to give (1R,2R)-2-(4-fluorophenyl)-N-methoxy-N-methylcyclopropane carboxamide (analytical ChiralPak AD-H, 5 μm, 4.6×100 mm, 10% ethanol/heptane, 2 mL/min, Rt=8.608 min, 100%, 410 mg) and (1S,2S)-2-(4-fluorophenyl)-N-methoxy-N-methyl cyclopropanecarboxamide (analytical ChiralPak AD-H, 5 μm, 4.6×100 mm, 10% ethanol/heptane, 2 mL/min, Rt=23.72, 2nd peak off of the chiral column, 400 mg).

INTERMEDIATE 11

(1S,2S)-1-(2-(4-Fluorophenyl)cyclopropyl)ethanone. Methylmagnesium bromide (0.717 mL, 3M in ether, 2.150 mmol) was added dropwise to a 0° C. solution of (1S,2S)-2-(4-fluorophenyl)-N-methoxy-N-methyl cyclopropanecarboxamide (400 mg, 1.792 mmol) in THF (15 mL). After 2 h, an additional equivalent of methylmagnesium bromide (0.717 mL, 2.150 mmol) was added. The reaction was slowly quenched with sat'd ammonium chloride (2 mL). The mixture was diluted with EtOAc, washed with $H_2O$, washed with brine, dried over magnesium sulfate, and concentrated to give (1S,2S)-1-(2-(4-fluorophenyl)cyclopropyl)ethanone as a slightly colored oil (304 mg, 95%). $^1$H NMR (500 MHz, CHLOROFORM-d) δ 7.12-7.04 (m, 2H), 7.03-6.95 (m, 2H), 2.53 (ddd, J=9.1, 6.5, 4.0 Hz, 1H), 2.37-2.30 (m, 3H), 2.18 (ddd, J=8.2, 5.1, 4.0 Hz, 1H), 1.67 (ddd, J=9.2, 5.1, 4.3 Hz, 1H), 1.35 (ddd, J=8.1, 6.6, 4.3 Hz, 1H).

INTERMEDIATE 12

(1R,2R)-1-(2-(4-Fluorophenyl)cyclopropyl)ethanone. (1R,2R)-2-(4-fluorophenyl)-N-methoxy-N-methyl cyclopropanecarboxamide (410 mg, 1.837 mmol) was reacted in a similar manner to the example above to give (1R,2R)-1-(2-(4-fluorophenyl)cyclopropyl)ethanone as a clear oil (300 mg, 92%). $^1$H NMR (500 MHz, CHLOROFORM-d) δ 7.11-7.05 (m, 2H), 7.03-6.95 (m, 2H), 2.53 (ddd, J=9.1, 6.5, 4.0 Hz, 1H), 2.33 (s, 3H), 2.18 (ddd, J=8.2, 5.1, 4.1 Hz, 1H), 1.67 (ddd, J=9.2, 5.1, 4.3 Hz, 1H), 1.35 (ddd, J=8.1, 6.6, 4.3 Hz, 1H).

INTERMEDIATE 13

1-((1S,2S)-2-(4-fluorophenyl)cyclopropyl)ethanamine, HCl. A soln of (1S,2S)-1-(2-(4-fluorophenyl)cyclopropyl) ethanone (304 mg, 1.706 mmol) in 7 M ammonia in MeOH (1219 µl, 8.53 mmol) was treated with titanium(IV) isopropoxide (1000 µl, 3.41 mmol) in one portion. The reaction was stirred for 6 h. The reaction was quenched with 25% ammonia, and the mixture was filtered. The solid was washed with EtOAc. The combined filtrates were extracted with 1N HCl (3x). The acidic extracts were made basic with 10% sodium hydroxide, and then extracted with dichloromethane (4x). The dichloromethane extracts were dried over potassium carbonate and concentrated to give a clear oil. The oil was dissolved in MeOH and treated with 2N HCl in ether to give a precipitate that was filtered and dried to give diasteromeric 1-((1S,2S)-2-(4-fluorophenyl)cyclopropyl)ethanamine, HCl, as a white solid (111 mg, 28.7%). $^1$H NMR (400 MHz, DMSO-$d_6$) δ 7.26-7.03 (m, 4H), 2.90-2.55 (m, 1H), 2.17-2.07 (m, 1H), 2.07-1.95 (m, 1H), 1.30 (dd, J=6.3, 4.5 Hz, 3H), 1.22-0.92 (m, 4H).

INTERMEDIATE 14

1-((1R,2R)-2-(4-fluorophenyl)cyclopropyl)ethanamine, HCl. (1R,2R)-1-(2-(4-Fluorophenyl)cyclopropyl)ethanone (325 mg, 1.824 mmol) was reacted in a similar manner to the example above to give diasteromeric 1-((1R,2R)-2-(4-fluorophenyl)cyclopropyl)ethanamine, HCl, as a white solid (133 mg, 41%). $^1$H NMR (400 MHz, DMSO-$d_6$) δ 7.26-7.03 (m, 4H), 2.90-2.55 (m, 1H), 2.17-2.07 (m, 1H), 2.07-1.95 (m, 1H), 1.30 (dd, J=6.3, 4.5 Hz, 3H), 1.22-0.92 (m, 4H).

INTERMEDIATE 15

2-phenylcyclopentanecarboxamide. A solution of 2-phenylcyclopentanecarboxylic acid (1 g, 5.26 mmol) and thionyl chloride (2 mL, 27.4 mmol) in dichloromethane (5 mL) was heated to reflux for 1 h. The reaction was concentrated to give the acid chloride clear oil. A solution of the acid chloride toluene was cooled in an ice bath and treated with ammonium hydroxide (2 mL, 51.4 mmol). The mixture was stirred for 1 h. The mixture was diluted with EtOAc, washed twice with $H_2O$, washed with brine, dried over magnesium sulfate, and concentrated to give 2-phenylcyclopentane carboxamide as a white waxy solid. (970 mg, 98%). $^1$H NMR (400 MHz, CHLOROFORM-d) δ 7.39-7.20 (m, 5H), 5.12 (br. s., 1H), 5.07 (br. s., 1H), 3.26 (td, J=9.9, 7.8 Hz, 1H), 2.73-2.59 (m, 1H), 2.31-2.03 (m, 3H), 1.98-1.72 (m, 3H).). LCMS: M+1=190.17.

INTERMEDIATE 16

(2-phenylcyclopentyl)methanamine. A solution of 2-phenylcyclopentane carboxamide (900 mg, 4.76 mmol) in THF (15 mL) was added dropwise to a cold (0° C.) suspension of LAH (271 mg, 7.13 mmol) in THF (15 mL). The cooling bath was removed and the mixture was stirred for 2.5 h. The reaction was quenched with MeOH (2 mL) and then 1N HCl (2 mL). The mixture was filtered through Celite. The filtrate was diluted with EtOAc and washed with sat'd sodium bicarbonate (3x), washed with brine, dried over potassium carbonate. and concentrated to give (2-phenylcyclopentyl)methanamine as a clear oil. (760 mg, 91.2%). $^1$H NMR (400 MHz, CHLOROFORM-d) δ 7.37-7.14 (m, 5H), 2.76 (dd, J=12.5, 4.8 Hz, 1H), 2.67-2.51 (m, 2H), 2.18-1.96 (m, 3H), 1.92-1.65 (m, 3H), 1.53-1.33 (m, 3H). LCMS: M+1=176.18.

INTERMEDIATE 17

2-Chloro-N-(3-phenylpropyl)-3-(trifluoromethyl)pyridin-4-amine. To a mixture of 2,4-dichloro-3-(trifluoromethyl) pyridine (197 mg, 0.912 mmol) and 3-aminopropylbenzene (0.136 mL, 0.925 mmol) was added acetonitrile (8.0 mL) and triethylamine (0.153 mL, 1.095 mmol). The mixture was heated to 80° C. After five hours the mixture was removed from heat and concentrated. This material was purified on silica gel (25 g) equilibrated in hexane, loaded in dichloromethane and eluted using hexane (96 mL) 0 to 30% EtOAc/hexane (600 mL, linear gradient). Early eluting fractions gave 51 mg of a pale yellow film as a 1:1 mixture of the minor 2-isomer and pyridine starting material by $^1$H NMR. Later eluting fractions gave 172 mg of a pale yellow film. This was consistent with the desired product by $^1$H NMR (400 MHz, CHLOROFORM-d) δ 8.02 (d, J=6.0 Hz, 1H), 7.37-7.29 (m, 2H), 7.27-7.17 (m, 3H), 6.45 (d, J=6.0 Hz, 1H), 5.52-5.31 (m, 1H), 3.27-3.16 (m, 2H), 2.75 (t, J=7.4 Hz, 2H), 2.02 (quin, J=7.3 Hz, 2H).

INTERMEDIATE 18

2-Azido-N-(3-phenylpropyl)-3-(trifluoromethyl)pyridin-4-amine. To a solution of 2-chloro-N-(3-phenylpropyl)-3-(trifluoromethyl)pyridin-4-amine (141 mg, 0.448 mmol) in DMF (2.5 mL) was added sodium azide (58.2 mg, 0.896 mmol) and ammonium chloride (47.9 mg, 0.896 mmol) was added and the mixture was heated to 100° C. for 22 hours. The mixture was cooled, quenched with sat'd aqueous $NaHCO_3$ solution then diluted with EtOAc and brine. The layers were shaken and separated. The aqueous portion was extracted with EtOAc and the combined organics were washed twice with brine, dried over $MgSO_4$, filtered and concentrated to give 198 mg of a yellow oil. This material was purified on silica gel (25 g) equilibrated in hexane, loaded in dichloromethane and eluted using hexane (96 mL), 20% EtOAc/hexane (250 mL), 20 to 50% EtOAc/hexane (500 mL, linear gradient) to give 125 mg of a clear film that was consistent with the desired product by $^1$H NMR and LC/MS (320/322, [M−H]−/[M+H]+). $^1$H NMR (400 MHz, CHLOROFORM-d) δ 8.59 (d, J=7.5 Hz, 1H), 7.38-7.30 (m, 2H), 7.28-7.17 (m, 3H), 6.71 (d, J=7.8 Hz, 1H), 5.52 (br. s., 1H), 3.40 (q, J=6.8 Hz, 2H), 2.78 (t, J=7.3 Hz, 2H), 2.08 (quin, J=7.3 Hz, 2H).

INTERMEDIATE 19

N4-(3-Phenylpropyl)-3-(trifluoromethyl)pyridine-2,4-diamine. To a solution of 2-azido-N-(3-phenylpropyl)-3-(trifluoromethyl)pyridin-4-amine (125 mg, 0.389 mmol) in tetrahydrofuran (4.0 mL) and water (0.066 mL, 3.69 mmol was added trimethylphosphine (1.0 M in tetrahydrofuran; 0.443 mL, 0.443 mmol. After four hours starting material remained and an additional 500 µL of trimethylphosphine was added. After 21 hours, LC/MS showed a 6.7:1 ratio of desired:starting material. An additional 200 µL of trimethylphosphine was added. After 25 hours the ratio by LC/MS was 12:1 product: starting material. After 27 hours the mixture was concentrated. This material was purified on silica gel (12 g) equilibrated in hexane, loaded in dichloromethane and eluted using hexane (96 mL), 20% EtOAc/hexane (250 mL), 20 to 50% EtOAc/hexane (320 mL, linear gradient). Fractions 39-50 gave 84.5 mg of an off white crystalline solid. This was consistent with desired product by $^1$H NMR containing 10% of the starting azide. The material was used as is. $^1$H NMR (400 MHz, CHLOROFORM-d) δ 7.79 (d, J=6.0 Hz, 1H), 7.39-7.29 (m, 2H), 7.25-7.15 (m, 3H), 5.98 (d, J=6.0 Hz, 1H), 4.96 (br. s., 3H), 3.25-3.12 (m, 2H), 2.73 (t, J=7.5 Hz, 2H), 1.98 (quin, J=7.3 Hz, 2H).

INTERMEDIATE 20

2-Bromo-4-((3-phenylpropyl)amino)nicotinonitrile. Prepared according to the methods above using 2,4-dibromonicotinonitrile (100 mg, 0.382 mmol), 3-aminopropylbenzene (0.058 mL, 0.401 mmol) and Hunig's Base (0.080 mL, 0.458 mmol) in DMF (1.5 mL) to give the desired product as a white solid (79 mg). LC/MS (316/318, [M−H]−/[M+H]+); $^1$H NMR (400 MHz, CHLOROFORM-d) δ 8.02 (dd, J=6.0, 0.5 Hz, 1H), 7.37-7.30 (m, 2H), 7.28-7.15 (m, 3H), 6.42 (d, J=6.0 Hz, 1H), 5.26 (br. s., 1H), 3.28 (td, J=7.0, 5.8 Hz, 2H), 2.75 (t, J=7.4 Hz, 2H), 2.03 (quin, J=7.3 Hz, 2H).

INTERMEDIATE 21

2-Azido-4-((3-phenylpropyl)amino)nicotinonitrile. Prepared according to the methods above using 2-bromo-4-((3-phenylpropyl)amino)nicotinonitrile (43.6 mg, 0.138 mmol), sodium azide (17.93 mg, 0.276 mmol) and ammonium chloride (14.75 mg, 0.276 mmol) in DMF (0.5 mL) at 100° C. for 18 hours to give the desired product as a yellow oil (35 mg). LC/MS (277, [M−H]−). This material was used as is.

INTERMEDIATE 22

2-Amino-4-((3-phenylpropyl)amino)nicotinonitrile. Prepared according to the methods above using 2-azido-4-((3-phenylpropyl)amino)nicotinonitrile (35 mg, 0.126 mmol) in tetrahydrofuran (1.5 mL), trimethylphosphine 1.0 M in tetrahydrofuran (0.629 mL, 0.629 mmol) and water (0.011 mL, 0.629 mmol) at rt for 3.5 hours to give the desired product as an off-white solid (11 mg). LC/MS (253, [M+H]); $^1$H NMR (400 MHz, CHLOROFORM-d) δ 7.85-7.78 (m, 1H), 7.37-7.29 (m, 2H), 7.26-7.23 (m, 1H), 7.22-7.16 (m, 2H), 5.92 (d, J=6.0 Hz, 1H), 5.17 (br. s., 2H), 4.94 (br. s., 1H), 3.30-3.20 (m, 2H), 2.74 (t, J=7.5 Hz, 2H), 2.00 (quin, J=7.3 Hz, 2H).

INTERMEDIATE 23

(S)-2-Bromo-4-((4-phenylbutan-2-yl)amino)nicotinonitrile. Prepared according to the methods above using 2,4-dibromonicotinonitrile (100 mg, 0.382 mmol), (S)-1-Methyl-3-phenyl-propylamine (58.1 mg, 0.382 mmol) and Hunig's Base (0.080 mL, 0.458 mmol) in DMF (1.5 mL) at 120° C. for 30 min to give the desired product as a clear oil (76 mg). LC/MS (316/318, [M−H]/[M+H]+); $^1$H NMR (400 MHz, CHLOROFORM-d) δ 8.05 (d, J=5.5 Hz, 1H), 7.33-7.25 (m, 2H), 7.23-7.15 (m, 3H), 6.81 (d, J=5.3 Hz, 1H), 5.06 (br. s., 1H), 4.33 (dt, J=14.0, 6.9 Hz, 1H), 2.71 (t, J=8.0 Hz, 2H), 1.98-1.83 (m, 2H), 1.32-1.25 (m, 3H).

INTERMEDIATE 24

(S)-2-Azido-4-((4-phenylbutan-2-yl)amino)nicotinonitrile. Prepared according to the methods above using (S)-2-bromo-4-((4-phenylbutan-2-yl)amino)nicotinonitrile (76.1 mg, 0.230 mmol), sodium azide (30.0 mg, 0.461 mmol) and ammonium chloride (24.65 mg, 0.461 mmol) in DMF (1.0 mL) at 100° C. for 2.5 hours to give the desired product as a yellow oil (59 mg). LC/MS (291/293, [M−H]−/[M+H]+).

INTERMEDIATE 25

(S)-2-Amino-4-((4-phenylbutan-2-yl)amino)nicotinonitrile. Prepared according to the methods above using (S)-2-azido-4-((4-phenylbutan-2-yl)amino)nicotinonitrile (59.1 mg, 0.192 mmol) in THF (2.0 mL), trimethylphosphine 1.0 M in tetrahydrofuran (0.960 mL, 0.960 mmol) and water (0.017 mL, 0.960 mmol) at rt for 3.5 hours to give the desired product as a white solid (35 mg). LC/MS (267, [M+H]+); $^1$H NMR (400 MHz, CHLOROFORM-d) δ 7.78 (d, J=6.3 Hz, 1H), 7.35-7.26 (m, 2H), 7.26-7.19 (m, 1H), 7.19-7.11 (m, 2H), 5.83 (d, J=6.3 Hz, 1H), 5.13 (br. s., 2H), 4.70 (d, J=8.0 Hz, 1H), 3.65-3.51 (m, 1H), 2.71 (t, J=7.7 Hz, 2H), 1.98-1.80 (m, 2H), 1.32-1.23 (m, 3H).

INTERMEDIATE 26

2-Bromo-3-cyclopropylpropanal. A solution of 3-cyclopropylpropanal (0.662 g, 6.75 mmol) in diethyl ether (15 mL) was cooled in an ice water bath and bromine (0.348 mL, 6.75 mmol) was added. After 15 min the cooling bath was removed. After 1 h an aliquot was removed, diluted with diethyl ether and washed with sat'd aqueous NaHCO$_3$, dried over Na$_2$SO$_4$ and carefully concentrated. $^1$H NMR showed near complete conversion of starting material to desired product (~4% starting material). The reaction was worked in the same way and carefully concentrated. Upon concentration, there appeared to be residual water present in the crude oil. The product was diluted with diethyl ether and further dried over MgSO$_4$, filtered and concentrated to give a yellow oil which was used as is. $^1$H NMR (400 MHz, CHLOROFORM-d) δ 9.47 (d, J=3.3 Hz, 1H), 4.31 (td, J=7.1, 3.1 Hz, 1H), 1.93 (t, J=7.0 Hz, 2H), 0.94-0.81 (m, 1H), 0.64-0.48 (m, 2H), 0.15-0.01 (m, 2H).

INTERMEDIATE 27

(E)-(3-(((Benzyloxy)carbonyl)amino)prop-1-en-1-yl)boronic acid. A solution of cyclohexene (8.5 mL, 84 mmol) and borane dimethylsulfide (10.5 mL, 105 mmol) in dry ether (90 mL) at 0° C. was stirred for 3 h. The solvent was removed by syringe, and the precipitate was washed with ether. The precipitate was suspended in THF (50 mL) and a solution of benzyl prop-2-yn-1-ylcarbamate (7.912 g, 41.8 mmol) in THF (50 mL) was added at 0° C. The resulting mixture was stirred at rt for 1 hr. To the mixture was added trimethylamine N-oxide dihydrate (13.94 g, 125 mmol) and the mixture was stirred at rt for 16 hr. The mixture was quenched with 2N HCl. The organic layer was separated and the aqueous layer was extracted with ether. The combined organic layers were extracted three times with 10% aqueous NaOH. The combined aqueous layers were washed with ether and made acidic with 2N HCl to give (E)-(3-(((benzyloxy)carbonyl)amino) prop-1-en-1-yl)boronic acid as a precipitate that was filtered and air dried to white solid (2.38 g, 24%). The material was used without purification.

INTERMEDIATE 28

(E)-benzyl (3-(4,4,5,5-tetramethyl-1,3,2-dioxaborolan-2-yl)allyl)carbamate. A mixture of (E)-(3-(((benzyloxy)carbonyl)amino)prop-1-en-1-yl)boronic acid (2.38 g, 10.14 mmol), pinacol (1.418 g, 12 mmol), and magnesium sulfate (2 g, 16.62 mmol) in ether (25 mL) was stirred for 2 days. The mixture was filtered and concentrated. The crude material was purified by silica gel chromatography using 0-30% EtOAc/hexane as the eluent to give (E)-benzyl (3-(4,4,5,5-tetramethyl-1,3,2-dioxaborolan-2-yl)allyl)carbamate as a clear oil (1.6 g, 50%). LCMS: Rt=3.66 min, 77%, (M+H)+=318, (M−H)−=316.

INTERMEDIATE 29

Benzyl ((2-(4,4,5,5-tetramethyl-1,3,2-dioxaborolan-2-yl) cyclopropyl)methyl)carbamate. A solution of diethylzinc (7.57 mL, 7.57 mmol) in dichloromethane (10 mL) was stirred at −78° C. under nitrogen as a solution of diiodomethane (1.22 mL, 15.1 mmol) in dichloromethane (10 mL) was added. The resulting mixture was stirred at −15° C. under nitrogen for 1 h to give a white milky suspension. A solution of (E)-benzyl (3-(4,4,5,5-tetramethyl-1,3,2-dioxaborolan-2-yl)allyl)carbamate (1.2 g, 3.78 mmol) in dichloromethane (10 mL) was added. The reaction mixture was stirred at rt for 1 h. and was then quenched with 1HCl. The dichloromethane layer was separated. The aqueous layer was extracted with dichloromethane (2×20 mL). The combined organic layers were washed with aqueous sodium bicarbonate (2×20 mL) and brine (20 mL), dried over magnesium sulfate, and concentrated. The residue was purified by silica gel chromatography using 0-30% EtOAc/hexane as the eluent to give benzyl ((2-(4,4,5,5-tetramethyl-1,3,2-dioxaborolan-2-yl)cyclopropyl)methyl)carbamate as a colorless oil (0.84 g, 60%). $^1$H NMR (400 MHz, METHANOL-d$_4$) δ 7.42-7.22 (m, 5H), 5.07 (s, 2H), 3.12-2.84 (m, 2H), 1.20 (s, 12H), 1.17-1.12 (m, 1H), 0.71-0.60 (m, 1H), 0.58-0.44 (m, 1H), −0.28 (dt, J=9.5, 5.8 Hz, 1H). M+1=332.2.

INTERMEDIATE 30

Benzyl ((2-(5-fluoropyrimidin-2-yl)cyclopropyl)methyl) carbamate. A mixture of benzyl ((2-(4,4,5,5-tetramethyl-1,3, 2-dioxaborolan-2-yl)cyclopropyl)methyl)carbamate (500 mg, 1.510 mmol), 2-chloro-5-fluoropyrimidine (45 mg, 0.340 mmol), potassium carbonate (100 mg, 0.724 mmol), and tetrakis(triphenylphosphine) palladium (0) (10 mg, 8.65 μmol) in dioxane (2 mL) and water (0.4 mL) was heated to 100° C. in a sealed vial for 16 h. The mixture was diluted with EtOAc and washed with sat'd sodium carbonate. The EtOAc layer was concentrated to an amber oil. The crude product was purified by silica gel chromatography using 0-30% EtOAc/hexane as the eluent to give benzyl ((2-(5-fluoropyrimidin-2-yl)cyclopropyl)methyl)carbamate as a colorless oil (220 mg, 42%). $^1$H NMR (400 MHz, CHLOROFORM-d) d 8.45-8.31 (m, 2H), 7.36-7.30 (m, 5H), 5.10 (s, 2H), 4.07 (br. s., 1H, NH), 3.39-3.15 (m, 2H), 2.19 (dt, J=8.5, 4.4 Hz, 1H), 1.78-1.62 (m, 1H), 1.31 (dt, J=8.7, 4.5 Hz, 1H), 1.09-0.95 (m, 1H). LCMS: M+1=302.2.

INTERMEDIATE 31

(2-(5-Fluoropyrimidin-2-yl)cyclopropyl)methanamine. A mixture of benzyl ((2-(5-fluoropyrimidin-2-yl)cyclopropyl) methyl)carbamate (180 mg, 0.597 mmol), 10% palladium on carbon (63 mg) in MeOH (10 mL) was shaken in a Parr shaker under hydrogen (10 psi) for 2 h. The reaction mixture was filtered and the filtrate was concentrated. The residue purified by silica gel chromatography using 0-20% 2.0 M ammonia in MeOH/EtOAc as the eluent to give (2-(5-fluoropyrimidin-2-yl)cyclopropyl)methanamine as a yellowish oil (48 mg, 48%). $^1$H NMR (400 MHz, CHLOROFORM-d) d 8.40 (s, 2H), 2.81-2.66 (m, 2H), 2.11 (dt, J=8.5, 4.4 Hz, 1H), 1.70-1.58 (m, 1H), 1.30 (bs, 2H, NH$_2$), 1.28 (m, 1H), 0.97 (ddd, J=8.5, 6.0, 4.3 Hz, 1H). LCMS: M+1=168.

INTERMEDIATE 32

(E)-3-(2-cyanophenyl)acrylic acid. A solution of 2-formylbenzonitrile (4.17 g, 31.8 mmol), malonic acid (7.61 g, 73.1 mmol), and piperidine (0.314 mL, 3.18 mmol) in pyridine (40 mL) was heated to reflux for 2 hr. The solution was cooled and poured into crushed ice (150 mL) and 12N HCl (30 mL). The white precipitate was filtered, washed with water, and air dried to give a tan powder (3.85 g, 70%). $^1$H NMR (500 MHz, DMSO-d6) δ 12.81 (br. s., 1H), 8.09 (d, J=7.9 Hz, 1H), 7.93 (dd, J=7.8, 0.9 Hz, 1H), 7.80-7.74 (m, 2H), 7.62 (td, J=7.6, 0.9 Hz, 1H), 6.80 (d, J=15.9 Hz, 1H).

INTERMEDIATE 33

(E)-3-(2-cyanophenyl)-N-methoxy-N-methylacrylamide. A suspension of (E)-3-(2-cyanophenyl)acrylic acid (3 g, 17.32 mmol) and thionyl chloride (6.0 mL, 82 mmol) in methylene chloride (10 mL) and DMF (1 drop) was then stirred at rt for 1 hr. The solution was then concentrated to a clear oil. A solution of the resulting acid chloride in methylene chloride (50 mL) was cooled in an ice bath. A solution of N,O-dimethylhydroxylamine, HCl (2.028 g, 20.79 mmol) and pyridine (5.60 mL, 69.3 mmol) in methylene chloride (50 mL). The ice bath was removed and the light yellow suspension was stirred at rt for 1 hr. The mixture was diluted with methylene chloride, washed with water and 1N HCl, dried over magnesium sulfate, and concentrated to give a light red oil. The oil was purified on silica gel using 20%-30% EtOAc/ hexanes to give (E)-3-(2-cyanophenyl)-N-methoxy-N-methylacrylamide (96930-078) as a red oil (3.4 g, 91%) which crystallized upon standing. $^1$H NMR (400 MHz, CHLOROFORM-d) δ 7.96 (d, J=15.8 Hz, 1H), 7.79-7.69 (m, 2H), 7.64 (td, J=7.8, 1.0 Hz, 1H), 7.54-7.42 (m, 1H), 7.34 (d, J=15.8 Hz, 1H), 3.82 (s, 3H), 3.35 (s, 3H). LCMS: M+1=217.0.

INTERMEDIATE 34

Trans-2-(2-cyanophenyl)-N-methoxy-N-methylcyclopropanecarboxamide. (E)-3-(2-cyanophenyl)-N-methoxy-N- methylacrylamide (3.4 g, 15.72 mmol) was cyclopropanated in a manner similar to Intermediate 9. The crude material was purified by on silica gel using 20-30% EtOAc/hexanes as the eluent to give 2-(2-cyanophenyl)-N-methoxy-N-methylcyclopropanecarboxamide as an oil (3.1 g, 86%). $^1$H NMR (400 MHz, CHLOROFORM-d) δ 7.65 (dd, J=7.7, 1.1 Hz, 1H), 7.54 (td, J=7.7, 1.4 Hz, 1H), 7.33 (td, J=7.7, 1.0 Hz, 1H), 7.16 (d, J=8.0 Hz, 1H), 3.81-3.74 (m, 3H), 3.29 (s, 3H), 2.85 (ddd, J=9.1, 6.3, 4.4 Hz, 1H), 2.53 (br. s., 1H), 1.84-1.72 (m, 1H), 1.40 (ddd, J=8.5, 6.3, 4.3 Hz, 1H). LCMS: M+1=231.0.

INTERMEDIATE 35

2-(2-formylcyclopropyl)benzonitrile. A solution of 2-(2-cyanophenyl)-N-methoxy-N-methylcyclopropanecarboxamide (250 mg, 1.086 mmol) in THF (5 mL) was stirred, maintaining the temperature below −40° C., as a suspension of LAH (82 mg, 2.171 mmol) in THF (20 mL) at −50° C. was added. After the addition was complete, the reaction was slowly allowed to warm to −30° C., and then cooled to below −40° C. The reaction was quenched with a EtOAc, followed by 1 N sodium hydroxide (1 mL). The reaction was stirred at rt for 30 min. The solution was diluted with EtOAc, filtered through celite, then concentrated. The material was purified on silica gel using 5-40% EtOAc/hexanes as the eluent to give 2-(2-formylcyclopropyl)benzonitrile (135 mg, 72.6%) as an oil. $^1$H NMR (400 MHz, CHLOROFORM-d) δ 9.42 (d, J=4.3 Hz, 1H), 7.67 (dd, J=7.8, 1.0 Hz, 1H), 7.56 (td, J=7.8, 1.3 Hz, 1H), 7.36 (td, J=7.6, 1.1 Hz, 1H), 7.12 (d, J=8.0 Hz, 1H), 2.95 (ddd, J=9.2, 6.6, 4.3 Hz, 1H), 2.27 (ddt, J=8.5, 5.3, 4.3 Hz, 1H), 1.87 (dt, J=9.3, 5.3 Hz, 1H), 1.67-1.49 (m, 1H). LCMS: M+1=171.1.

INTERMEDIATE 36

2-(2-(Hydroxymethyl)cyclopropyl)benzonitrile. Solid sodium borohydride (110 mg, 2.92 mmol) was added portionwise to a solution of 2-(2-formylcyclopropyl)benzonitrile (500 mg, 2.92 mmol) in methylene chloride (6 mL) and MeOH (10 mL). The mixture was stirred for 2 hr. The reaction was concentrated, and the residue was dissolved in ether and water. The ether layer was separated, washed with water and brine, dried over magnesium sulfate, and concentrated to give 2-(2-(hydroxymethyl)cyclopropyl)benzonitrile as a slightly colored wax (425 mg, 84%). $^1$H NMR (400 MHz, CHLOROFORM-d) δ 7.63 (dd, J=7.7, 0.9 Hz, 1H), 7.52 (td, J=7.8, 1.0 Hz, 1H), 7.36-7.24 (m, 1H), 7.08 (d, J=8.0 Hz, 1H), 3.87-3.72 (m, 1H), 3.65 (dd, J=11.2, 7.2 Hz, 1H), 2.25-2.13 (m, 1H), 1.82 (br. s., 1H), 1.60 (s, 1H), 1.56-1.45 (m, 1H), 1.12 (ddt, J=15.3, 8.6, 5.3 Hz, 1H). LCMS: M+1=173.1.

INTERMEDIATE 37

2-(2-(Aminomethyl)cyclopropyl)benzonitrile. A cold solution of 2-(2-(hydroxymethyl)cyclopropyl)benzonitrile (425 mg, 2.454 mmol) in methylene chloride (15 mL), and triethyl amine (1.368 mL, 9.81 mmol) was treated with methanesulfonyl chloride (0.287 mL, 3.68 mmol) dropwise with ice bath cooling. The cooling bath was removed, the reaction warmed to rt for 1 hr. The reaction was diluted with methylene chloride washed with water and brine, dried over magnesium sulfate, and concentrated to give a wax. A solution of the material in acetonitrile (15 mL) and ammonium hydroxide (2 mL, 51.4 mmol) was stirred for 16 h at rt. The reaction was concentrated to about ½ volume and diluted with ether. The suspension was extracted with 1N HCl. The acid extracts were made basic with 50% sodium hydroxide, then extracted with methylene chloride (4×). The organics were dried potassium carbonate and concentrated. The resulting dark wax (400 mg) was then purified on silica gel using 1-20% MeOH/methylene chloride to give an orange wax. The wax was triturated with acetone to give 2-(2-(aminomethyl)cyclopropyl)benzonitrile as a white solid (55 mg, 13%). $^1$H NMR (400 MHz, DMSO-$d_6$) δ 7.91 (br. s., 2H), 7.80 (dd, J=7.8, 1.0 Hz, 1H), 7.65 (td, J=7.8, 1.3 Hz, 1H), 7.40 (td, J=7.6, 1.1 Hz, 1H), 7.20 (d, J=7.8 Hz, 1H), 2.97 (t, J=6.9 Hz, 2H), 2.32-2.19 (m, 1H), 1.68-1.48 (m, 1H), 1.23 (dt, J=8.8, 5.2 Hz, 1H), 1.10 (dt, J=8.7, 5.2 Hz, 1H). LCMS: M+1=173.05.

INTERMEDIATE 38

(2-(Pyridin-4-yl)cyclopropyl)methanamine, HCl. This intermediate was prepared from (E)-3-(pyridin-4-yl)acrylic acid in a manner similar to Intermediates 32-37 to give (2-(pyridin-4-yl)cyclopropyl)methanamine, HCl, as a white solid (26.7%). $^1$H NMR (400 MHz, DMSO-$d_6$) δ 8.74 (d, J=6.5 Hz, 2H), 8.25 (br. s., 2H), 7.77 (d, J=5.5 Hz, 2H), 3.17-3.00 (m, 1H), 2.77 (d, J=6.0 Hz, 1H), 2.41 (br. s., 1H), 1.70 (d, J=4.0 Hz, 1H), 1.53-1.36 (m, 2H).

INTERMEDIATE 39

(2-(pyridin-3-yl)cyclopropyl)methanamine, HCl. This intermediate was prepared from (E)-3-(pyridin-4-yl)acrylic acid in a manner similar to Intermediates 32-37 to give (2-(pyridin-3-yl)cyclopropyl)methanamine, HCl, as a white solid (36.4%). $^1$H NMR (400 MHz, DMSO-$d_6$) δ 8.80 (d, J=1.8 Hz, 1H), 8.69 (d, J=4.8 Hz, 1H), 8.29-8.12 (m, 3H), 7.87 (dd, J=7.9, 5.4 Hz, 1H), 3.08 (dt, J=12.7, 6.1 Hz, 1H), 2.82-2.64 (m, 1H), 2.33-2.19 (m, 1H), 1.56-1.41 (m, 1H), 1.35 (dt, J=8.8, 5.3 Hz, 1H), 1.22 (dt, J=8.8, 5.4 Hz, 1H).

INTERMEDIATE 40

N-(2,4-Dimethoxybenzyl)-1-(4-fluorophenyl)cyclopropanecarboxamide. A solution of 1-(4-fluorophenyl)cyclopropanecarboxylic acid (1.85 g, 10.27 mmol) in dichloromethane (25 mL) and a few drops of DMF was stirred at rt as oxalyl chloride (1.798 mL, 20.54 mmol) was added. The mixture was stirred at rt for 40 min and then concentrated. A solution of the residue and TEA (4.29 mL, 30.8 mmol) in methylene chloride (25 mL) was stirred at 0° C. as (2,4-dimethoxyphenyl)methanamine, HCl (2.509 g, 12.32 mmol) was added. The mixture was stirred at rt for 2 h and then filtered and concentrated. The residue was purified on silica gel chromatography 0-100% EtOAc/hexane as the eluent to give N-(2,4-dimethoxybenzyl)-1-(4-fluorophenyl)cyclopropanecarboxamide (3.3 g, 9.82 mmol, 96% yield) as white solid. $^1$H NMR (400 MHz, CHLOROFORM-d) δ 7.41-7.32 (m, 2H), 7.13-7.00 (m, 3H), 6.44-6.34 (m, 2H), 5.94 (br. s., 1H), 4.28 (d, J=5.8 Hz, 2H), 3.79 (s, 3H), 3.60 (s, 3H), 1.60 (q, J=3.6 Hz, 2H), 0.99 (q, J=3.8 Hz, 2H). LCMS: M+1=330.0.

INTERMEDIATE 41

1-(4-Fluorophenyl)cyclopropanecarboxamide. A mixture of N-(2,4-dimethoxybenzyl)-1-(4-fluorophenyl)cyclopropanecarboxamide (1.5 g, 4.55 mmol) and TFA (7.02 mL, 91 mmol) was stirred at rt for 2 h. The reaction mixture was concentrated under vacuum. The residue was suspended in EtOAc (20 mL) and sat'd aqueous sodium bicarbonate (20 mL). The suspension was filtered and the filter cake was washed with EtOAc. The EtOAc layer of the filtrate was separated and the aqueous layer was extracted with ethyl acetae (2×10 mL). The combined EtOAc layers layers were washed with aqueous sodium bicarbonate and brine, dried over magnesium sulfate, and concentrated. The residue was triturated with a minimum amount of MeOH to give 1-(4-fluorophenyl)cyclopropanecarboxamide (0.7 g, 3.71 mmol, 81% yield) as white solid. $^1$H NMR (400 MHz, CHLOROFORM-d) δ 7.48-7.37 (m, 2H), 7.12-7.02 (m, 2H), 5.70 (br. s., 1H), 5.28 (br. s., 1H), 1.63 (q, J=3.8 Hz, 2H), 1.07 (q, J=3.8 Hz, 2H). LCMS: M+1=180.0.

INTERMEDIATE 42

(1-(4-fluorophenyl)cyclopropyl)methanamine. LAH powder (0.153 g, 4.02 mmol) was added portionwise to a solution of 1-(4-fluorophenyl)cyclopropane carboxamide (0.6 g, 3.35 mmol) in THF (10 mL) at rt and the resulting mixture was heated to reflux for 1 h. The suspension was cooled to rt, quenched with MeOH (2 mL), and then 1N HCl (2 mL). The mixture was filtered through Celite, and the Celite washed with 1N HCl (2 mL). The filtrate was made basic with 50% NaOH, and extracted with EtOAc (3×10 mL). The organic extracts were washed with brine, dried over potassium carbonate, and concentrated. The residue was purified by silica gel chromatography using 0-20% 2M ammonia in MeOH/EtOAc as the eluent to give (1-(4-fluorophenyl)cyclopropyl) methanamine (0.5 g, 2.72 mmol, 81% yield) as a clear oil. $^1$H NMR (400 MHz, CHLOROFORM-d) δ 7.35-7.22 (m, 2H), 7.04-6.92 (m, 2H), 2.75 (s, 2H), 1.15 (br. s., 2H), 0.84-0.68 (m, 4H). LCMS: m+1=166.0.

EXAMPLE 1

Racemic trans 8-chloro-3-(cyclopropylmethyl)-N-((2-(4-fluorophenyl)cyclopropyl)methyl)-[1,2,4]triazolo[4,3-a]pyridin-7-amine. A mixture of (2-(4-fluorophenyl)cyclopropyl) methanamine, HCl (87 mg, 0.432 mmol), 8-chloro-3-(cyclopropylmethyl)-7-iodo-[1,2,4]triazolo[4,3-a]pyridine (120 mg, 0.360 mmol), Xantphos (10.41 mg, 0.018 mmol), tris(dibenzylideneaceton)-dipalladium (16.47 mg, 0.018 mmol) and potassium t-butoxide (121 mg, 1.079 mmol) in t-butanol (3 mL) was stirred at 90° C. under nitrogen for 1 h. The mixture was diluted with MeOH and purified by preparative HPLC on a Phenomenex-Luna 30×100 mm S10 Axia column using 10-90% water/MeOH/0.1% TFA as the eluent. The product fractions were combined and neutralized with sat'd aqueous sodium bicarbonate. The fractions were partially concentrated, and then extracted twice with EtOAc. The EtOAc extracts were washed with sat'd aqueous sodium bicarbonate and brine (10 mL), dried over magnesium sulfate, and concentrated to give 8-chloro-3-(cyclopropylmethyl)-N-((2-(4-fluorophenyl)cyclopropyl)methyl)-[1,2,4]triazolo[4,3-a]pyridin-7-amine (50 mg, 35.2% yield) as a white foamy solid. $^1$H NMR (400 MHz, METHANOL-d$_4$) δ 8.14 (d, J=7.5 Hz, 1H), 7.06 (dd, J=8.7, 5.4 Hz, 2H), 6.96-6.85 (m, 3H), 3.45 (d, J=6.5 Hz, 2H), 2.97 (d, J=6.8 Hz, 2H), 1.97-1.87 (m, 1H), 1.46-1.31 (m, 1H), 1.22-1.12 (m, 1H), 1.04-0.92 (m, 2H), 0.64-0.52 (m, 2H), 0.37-0.23 (m, 2H). LCMS: M+1=371.1.

EXAMPLE 2

8-Chloro-3-(cyclopropylmethyl)-N-(3-phenylcyclopentyl)-[1,2,4]triazolo[4,3-a]pyridin-7-amine. 3-Phenylcyclopentanamine was reacted in a manner similar to Example 1 to give 8-chloro-3-(cyclopropylmethyl)-N-(3-phenylcyclopentyl)-[1,2,4]triazolo[4,3-a]pyridin-7-amine as a clear wax (7% yield). $^1$H NMR (400 MHz, METHANOL-d$_4$) δ 8.46 (dd, J=7.8, 1.3 Hz, 1H), 7.40-7.13 (m, 6H), 4.40 (s, 1H), 3.42 (d, J=10.5 Hz, 1H), 3.23 (d, J=9.0 Hz, 1H), 3.04 (d, J=7.0 Hz, 2H), 2.67-2.56 (m, 1H), 2.47 (d, J=5.3 Hz, 1H), 2.33-2.11 (m, 1H), 2.01-1.74 (m, 2H), 1.38-1.18 (m, 1H), 0.77-0.64 (m, 2H), 0.46-0.34 (m, 2H). LCMS: M+1=367.2.

EXAMPLE 3

(+/−)Trans-8-chloro-3-(cyclopropylmethyl)-N-((2-phenylcyclopentyl)methyl)-[1,2,4]triazolo[4,3-a]pyridin-7-amine. (2-Phenylcyclopentyl)methylamine was reacted in a manner similar to Example 1 to give (+/−)-trans-8-chloro-3-(cyclopropylmethyl)-N-((2-phenylcyclopentyl)methyl)-[1,2,4]triazolo[4,3-a]pyridin-7-amine as a clear wax (18% yield). $^1$H NMR (400 MHz, METHANOL-d$_4$) δ 8.05 (d, J=7.5 Hz, 1H), 7.33-7.20 (m, 5H), 7.20-7.08 (m, 1H), 6.60 (d, J=7.8 Hz, 1H), 3.48-3.36 (m, 1H), 2.97 (d, J=7.0 Hz, 2H), 2.83-2.66 (m, 1H), 2.40 (d, J=8.0 Hz, 1H), 2.23-2.05 (m, 2H), 1.93-1.76 (m, 3H), 1.57 (dd, J=12.7, 7.2 Hz, 1H), 1.26-1.13 (m, 1H), 0.70-0.56 (m, 2H), 0.39-0.25 (m, 2H). LCMS: M+1=381.19.

EXAMPLE 4

Trans-8-chloro-3-(cyclopropylmethyl)-N-((2-phenylcyclopropyl)methyl)-[1,2,4]triazolo[4,3-a]pyridin-7-amine. Racemic (2-phenylcyclopropyl) methanamine, HCl, was reacted in a manner similar to Example 1 to give trans-8-chloro-3-(cyclopropylmethyl)-N-((2-phenylcyclopropyl) methyl)-[1,2,4]triazolo[4,3-a]pyridin-7-amine (10.9 mg, 33.7%). $^1$H NMR (500 MHz, DMSO-d$_6$) δ 8.21 (d, J=7.6 Hz, 1H), 7.21 (t, J=7.6 Hz, 2H), 7.10 (t, J=7.3 Hz, 1H), 7.04 (d, J=7.3 Hz, 2H), 6.90 (d, J=7.6 Hz, 1H), 6.42 (t, J=6.3 Hz, 1H), 3.42-3.37 (m, 2H), 2.94 (d, J=7.0 Hz, 2H), 1.97-1.88 (m, 1H), 1.40-1.27 (m, 1H), 1.18-1.07 (m, 1H), 1.04-0.95 (m, 1H), 0.95-0.88 (m, 1H), 0.52-0.43 (m, 2H), 0.24 (d, J=4.9 Hz, 2H). LCMS: M+1=353.1.

EXAMPLE 5

8-Chloro-3-(cyclopropylmethyl)-N-(((1S,2S)-2-(4-fluorophenyl)cyclopropyl)methyl)-[1,2,4]triazolo[4,3-a]pyridin-7-amine. (1S,2S)-2-(4-Fluorophenyl)cyclopropyl) methanamine HCl was reacted in a manner similar to Example 1 to give 8-chloro-3-(cyclopropylmethyl)-N-(((1S,2S)-2-(4-fluorophenyl)cyclopropyl)methyl)-[1,2,4]triazolo [4,3-a]pyridin-7-amine (19.6%) as a colorless film. $^1$H NMR (400 MHz, CHLOROFORM-d) δ 7.80 (d, J=7.5 Hz, 1H), 7.08-7.01 (m, 2H), 7.01-6.91 (m, 2H), 6.60 (d, J=7.5 Hz, 1H), 4.91 (br. s., 1H), 3.50-3.26 (m, 2H), 3.01 (d, J=6.8 Hz, 2H), 1.96-1.86 (m, 1H), 1.47-1.35 (m, 1H), 1.15 (dddd, J=6.5, 4.9, 3.3, 1.4 Hz, 1H), 1.08-0.94 (m, 2H), 0.64-0.55 (m, 2H), 0.39-0.26 (m, 2H) (HNMR showed there was some acetate from the HPLC solvent left).

EXAMPLE 6

Trans-8-chloro-3-(cyclopropylmethyl)-N-((2-(2-methoxyphenyl)cyclopropyl)methyl)-[1,2,4]triazolo[4,3-a]pyridin-7-amine. A mixture of 8-chloro-3-(cyclopropylmethyl)-7-iodo-[1,2,4]triazolo[4,3-a]pyridine (30 mg, 0.090 mmol) and trans-(2-(2-methoxyphenyl)cyclopropyl)methanamine, HCl (23.06 mg, 0.108 mmol) was reacted in a manner similar to Example 1 to give 8-chloro-3-(cyclopropylmethyl)-N-((2-(2-methoxyphenyl)cyclopropyl)methyl)-[1,2,4]triazolo[4,3-a] pyridin-7-amine as a film (5.5 mg, 15%). $^1$H NMR (500 MHz, DMSO-d$_6$) δ 8.25 (d, J=7.3 Hz, 1H), 7.13 (ddd, J=8.3, 6.5, 2.3 Hz, 1H), 6.95-6.88 (m, 2H), 6.87-6.77 (m, 2H), 6.25 (t, J=6.0

Hz, 1H), 3.49-3.42 (m, 1H), 3.42-3.36 (m, 1H), 2.96 (d, J=7.0 Hz, 2H), 2.15-2.03 (m, 1H), 1.36-1.24 (m, 1H), 1.21-1.06 (m, 1H), 0.93 (td, J=8.0, 5.6 Hz, 2H), 0.50 (dd, J=7.9, 1.5 Hz, 2H), 0.31-0.19 (m, 2H). LCMS: M+1=383.20.

EXAMPLE 7

Trans-8-chloro-3-(cyclopropylmethyl)-N-((2-(2-(difluoromethoxy)phenyl)cyclopropyl)methyl)-[1,2,4]triazolo[4,3-a]pyridin-7-amine. A mixture of 8-chloro-3-(cyclopropylmethyl)-7-iodo-[1,2,4]triazolo[4,3-a]pyridine (30 mg, 0.090 mmol) and trans-(2-(2-(difluoromethoxy)phenyl)cyclopropyl)methanamine, HCl (26.9 mg, 0.108 mmol) was reacted in a manner similar to Example 1 to give trans-8-chloro-3-(cyclopropylmethyl)-N-((2-(2-(difluoromethoxy)phenyl)cyclopropyl)methyl)-[1,2,4]triazolo[4,3-a]pyridin-7-amine as a film (12.7 mg, 32%). $^1$H NMR (500 MHz, DMSO-$d_6$) δ 8.24 (d, J=7.6 Hz, 1H), 7.21 (dd, J=7.6, 1.5 Hz, 1H), 7.19 (t, J=74.3 Hz, 1H), 7.17-7.11 (m, 2H), 6.98 (d, J=7.6 Hz, 1H), 6.93 (d, J=7.6 Hz, 1H), 6.38 (br. s., 1H), 3.60-3.45 (m, 1H), 3.45-3.38 (m, 1H), 2.96 (d, J=6.7 Hz, 2H), 2.15-2.04 (m, 1H), 1.49-1.37 (m, 1H), 1.20-1.10 (m, 1H), 1.09-1.01 (m, 1H), 1.00-0.90 (m, 1H), 0.50 (dd, J=7.9, 1.5 Hz, 2H), 0.26 (d, J=4.9 Hz, 2H). LCMS: M+1=419.2

EXAMPLE 8

8-Chloro-3-(cyclopropylmethyl)-N-(((1S,2S)-2-(3-methoxyphenyl)cyclopropyl)methyl)-[1,2,4]triazolo[4,3-a]pyridin-7-amine. A mixture of ((1S,2S)-2-(3-methoxyphenyl)cyclopropyl)methanamine, HCl (23.06 mg, 0.108 mmol) and 8-chloro-3-(cyclopropylmethyl)-7-iodo-[1,2,4]triazolo[4,3-a]pyridine (30 mg, 0.090 mmol) was reacted in a manner similar to Example 1 to give 8-chloro-3-(cyclopropylmethyl)-N-(((1S,2S)-2-(3-methoxyphenyl)cyclopropyl)methyl)-[1,2,4]triazolo[4,3-a]pyridin-7-amine (11% yield) as a colorless film. $^1$H NMR (400 MHz, CHLOROFORM-d) δ 7.90 (d, J=7.5 Hz, 1H), 7.20 (t, J=7.9 Hz, 1H), 6.73 (ddd, J=8.2, 2.6, 0.8 Hz, 1H), 6.70-6.64 (m, 2H), 6.64-6.61 (m, 1H), 5.12-5.01 (m, 1H), 3.80 (s, 3H), 3.50-3.29 (m, 2H), 3.03 (d, J=6.5 Hz, 2H), 1.91 (dt, J=9.0, 4.8 Hz, 1H), 1.52-1.38 (m, 1H), 1.22-0.97 (m, 3H), 0.67-0.56 (m, 2H), 0.37-0.27 (m, 2H). LCMS M+1=383.2

EXAMPLE 9

Trans-8-chloro-3-(cyclopropylmethyl)-N-((2-(2-(trifluoromethoxy)phenyl)cyclopropyl)methyl)-[1,2,4]triazolo[4,3-a]pyridin-7-amine. A mixture of 8-chloro-3-(cyclopropylmethyl)-7-iodo-[1,2,4]triazolo[4,3-a]pyridine (30 mg, 0.090 mmol) and trans-(2-(2-(trifluoromethoxy)phenyl)cyclopropyl)methanamine, HCl (28.9 mg, 0.108 mmol) was reacted in a manner similar to Example 1 to give trans-8-chloro-3-(cyclopropylmethyl)-N-((2-(2-(trifluoromethoxy)phenyl)cyclopropyl)methyl)-[1,2,4]triazolo[4,3-a]pyridin-7-amine as a film (30.3 mg, 73.3%). $^1$H NMR (500 MHz, DMSO-$d_6$) δ 8.24 (d, J=7.6 Hz, 1H), 7.33-7.21 (m, 3H), 7.08-7.01 (m, 1H), 6.92 (d, J=7.6 Hz, 1H), 6.37 (t, J=6.0 Hz, 1H), 3.56-3.38 (m, 2H), 2.96 (d, J=6.7 Hz, 2H), 2.15-2.05 (m, 1H), 1.55-1.44 (m, 1H), 1.19-1.07 (m, 2H), 1.04-0.94 (m, 1H), 0.50 (dd, J=8.1, 1.7 Hz, 2H), 0.26 (d, J=4.0 Hz, 2H). LCMS: M+1=437.2.

EXAMPLE 10

8-Chloro-3-(cyclopropylmethyl)-N-(((1S,2S)-2-(3,6-difluoro-2-methoxyphenyl)cyclopropyl)methyl)-[1,2,4]triazolo[4,3-a]pyridin-7-amine.((1S,2S)-2-(3,6-Difluoro-2-methoxyphenyl)cyclopropyl)methanamine, HCl, was reacted in a manner similar to Example 1 to give 8-chloro-3-(cyclopropyl methyl)-N-(((1S,2S)-2-(3,6-difluoro-2-methoxyphenyl)cyclopropyl)methyl)-[1,2,4]triazolo[4,3-a]pyridin-7-amine as a film (4.3 mg, 6.5%). $^1$H NMR (500 MHz, DMSO-$d_6$) δ 8.25 (d, J=7.6 Hz, 1H), 7.12 (td, J=10.0, 5.3 Hz, 1H), 6.90 (d, J=7.9 Hz, 2H), 6.34 (t, J=5.8 Hz, 1H), 3.84 (s, 3H), 3.58-3.45 (m, 1H), 3.36 (d, J=7.0 Hz, 1H), 2.95 (d, J=6.7 Hz, 2H), 1.98-1.82 (m, 1H), 1.64 (d, J=6.4 Hz, 1H), 1.19-1.05 (m, 2H), 1.05-0.94 (m, 1H), 0.50 (d, J=7.9 Hz, 2H), 0.25 (d, J=4.9 Hz, 2H). LCMS. M+1=419.3.

EXAMPLE 11

8-Chloro-3-(cyclopropylmethyl)-N-(((1S,2S)-2-(2,3-dihydrobenzofuran-4-yl)cyclopropyl)methyl)-[1,2,4]triazolo[4,3-a]pyridin-7-amine. ((1S,2S)-2-(2,3-Dihydrobenzofuran-4-yl)cyclopropyl)methanamine, HCl, was reacted in a manner similar to Example 1 to give 8-chloro-3-(cyclopropyl methyl)-N-(((1S,2S)-2-(2,3-dihydrobenzofuran-4-yl)cyclopropyl)methyl)-[1,2,4]triazolo[4,3-a]pyridin-7-amine as a film (12.4 mg, 21%). $^1$H NMR (500 MHz, DMSO-$d_6$) δ 8.23 (d, J=7.6 Hz, 1H), 6.94 (t, J=7.8 Hz, 1H), 6.91 (d, J=7.8 Hz, 1H), 6.52 (d, J=7.9 Hz, 1H), 6.42 (t, J=6.1 Hz, 1H, NH), 6.33 (d, J=7.9 Hz, 1H), 4.49 (dd, J=16.2, 7.6 Hz, 2H), 3.53-3.42 (m, 1H), 3.42-3.39 (m, 1H), 3.21-3.10 (m, 2H), 2.95 (d, J=6.7 Hz, 2H), 1.89-1.80 (m, 1H), 1.39-1.29 (m, 1H), 1.13 (d, J=6.7 Hz, 1H), 0.98 (t, J=7.0 Hz, 2H), 0.57-0.43 (m, 2H), 0.28-0.15 (m, 2H). LCMS: M+1=395.2.

EXAMPLE 12

8-Chloro-3-(cyclopropylmethyl)-N-((2-(5-fluoropyrimidin-2-yl)cyclopropyl)methyl)-[1,2,4]triazolo[4,3-a]pyridin-7-amine. (2-(5-Fluoropyrimidin-2-yl)cyclopropyl)methanamine, HCl, was reacted in a manner similar to Example 1 to give 8-chloro-3-(cyclopropylmethyl)-N-((2-(5-fluoropyrimidin-2-yl)cyclopropyl)methyl)-[1,2,4]triazolo[4,3-a]pyridin-7-amine as a film (8.5 mg, 37%). $^1$H NMR (500 MHz, DMSO-$d_6$) δ 8.68 (s, 2H), 8.22 (d, J=7.6 Hz, 1H), 6.91 (d, J=7.6 Hz, 1H), 6.54-6.38 (t, 1H, NH), 2.94 (d, J=6.4 Hz, 2H), 2.30 (br. s., 1H), 1.74 (br. s., 1H), 1.14 (t, J=6.3 Hz, 3H), 0.49 (d, J=7.6 Hz, 2H), 0.24 (d, J=4.6 Hz, 2H). LXMS: M+1=373.2.

EXAMPLE 13

3-(Cyclopropylmethyl)-N-((2-(5-fluoropyrimidin-2-yl)cyclopropyl)methyl)-8-(trifluoromethyl)-[1,2,4]triazolo[4,3-a]pyridin-7-amine. 7-Chloro-3-(cyclopropylmethyl)-8-(trifluoromethyl)-[1,2,4]triazolo[4,3-a]pyridine was reacted in a manner similar to Example 1 to give 3-(cyclopropyl methyl)-N-((2-(5-fluoropyrimidin-2-yl)cyclopropyl)methyl)-8-(trifluoromethyl)-[1,2,4]triazolo[4,3-a]pyridin-7-amine as a film (1 mg, 3.4%). $^1$H NMR (500 MHz, DMSO-$d_6$) δ 8.69 (s, 2H), 8.34 (d, J=7.9 Hz, 1H), 6.93 (d, J=7.6 Hz, 1H), 6.83 (br. s., 1H), 2.94 (d, J=6.7 Hz, 2H), 2.36-2.29 (m, 1H), 1.78-1.73 (m, 1H), 1.18-1.11 (m, 3H), 0.50 (dd, J=8.1, 1.7 Hz, 2H), 0.25 (d, J=4.9 Hz, 2H).

EXAMPLE 14

8-Chloro-3-(cyclopropylmethyl)-N-(1-((1R,2R)-2-(4-fluorophenyl)cyclopropyl)ethyl)-[1,2,4]triazolo[4,3-a]pyridin-7-amine. A mixture of 8-chloro-3-(cyclopropyl methyl)-7-iodo-[1,2,4]triazolo[4,3-a]pyridine (15 mg, 0.045 mmol) and 1-((1R,2R)-2-(4-fluorophenyl)cyclopropyl)ethanamine, HCl (11.64 mg, 0.054 mmol) was reacted in a manner similar to Example 1 to give 8-chloro-3-(cyclopropyl methyl)-N-(1-((1R,2R)-2-(4-fluorophenyl)cyclopropyl)ethyl)-[1,2,4]triazolo[4,3-a]pyridin-7-amine as a film (5.6 mg, 31%). $^1$H NMR (500 MHz, DMSO-d$_6$) δ 8.22 (dd, J=7.5, 4.1 Hz, 1H), 7.11-7.01 (m, 4H), 6.86 (dd, J=11.6, 7.6 Hz, 1H), 5.87-5.79 (m, 1H), 3.71-3.59 (m, 1H), 2.95 (d, J=6.7 Hz, 2H), 1.90-1.80 (m, 1H), 1.46-1.33 (m, 1H), 1.31 (d, J=6.4 Hz, 3H), 1.13 (d, J=7.0 Hz, 1H), 0.93-0.84 (m, 2H), 0.55-0.43 (m, 2H), 0.25 (d, J=4.9 Hz, 2H). LCMS: M+1=385.2. Two peaks were observed.

EXAMPLE 15

8-Chloro-3-(cyclopropylmethyl)-N-(1-((1S,2S)-2-(4-fluorophenyl)cyclopropyl)ethyl)-[1,2,4]triazolo[4,3-a]pyridin-7-amine. A mixture of 8-chloro-3-(cyclopropylmethyl)-7-iodo-[1,2,4]triazolo[4,3-a]pyridine (15 mg, 0.045 mmol) and 1-((1S,2S)-2-(4-fluorophenyl)cyclopropyl)ethanamine, HCl (11.64 mg, 0.054 mmol) was reacted in a manner similar to Example 1 to give 8-chloro-3-(cyclopropylmethyl)-N-(1-((1S,2S)-2-(4-fluorophenyl)cyclopropyl)ethyl)-[1,2,4]triazolo[4,3-a]pyridin-7-amine as a film (7.6 mg, 43%). $^1$H NMR (500 MHz, DMSO-d$_6$) δ 8.22 (dd, J=7.5, 3.8 Hz, 1H), 7.15-6.98 (m, 4H), 6.86 (dd, J=11.0, 7.9 Hz, 1H), 5.82 (t, J=9.8 Hz, 1H), 3.56 (d, J=7.9 Hz, 2H), 2.95 (d, J=6.7 Hz, 2H), 2.02-1.95 (m, 1H), 1.31 (d, J=4.9 Hz, 3H), 1.15 (d, J=7.0 Hz, 1H), 0.93-0.84 (m, 2H), 0.54-0.44 (m, 2H), 0.25 (d, J=4.6 Hz, 2H). LCMS: M+1=385.2. Two peaks of 55/45 corresponding to the two diastereomers were observed.

EXAMPLE 16

8-chloro-3-(cyclopropylmethyl)-N-((1-(4-fluorophenyl)cyclopropyl)methyl)-[1,2,4]triazolo[4,3-a]pyridin-7-amine. A mixture of 8-chloro-3-(cyclopropylmethyl)-7-iodo-[1,2,4]triazolo[4,3-a]pyridine and 8-chloro-3-(cyclopropylmethyl)-7-iodo-[1,2,4]triazolo[4,3-a]pyridine (50 mg, 0.150 mmol) was reacted in a manner similar to Example 1 to give 8-chloro-3-(cyclopropylmethyl)-N-((1-(4-fluorophenyl)cyclopropyl)methyl)-[1,2,4]triazolo[4,3-a]pyridin-7-amine as a white solid (20 mg, 35.3%). $^1$H NMR (400 MHz, METHANOL-d$_4$) δ 7.95 (d, J=7.8 Hz, 1H), 7.44-7.30 (m, 2H), 6.95 (t, J=8.9 Hz, 2H), 6.54 (d, J=7.8 Hz, 1H), 3.57 (s, 2H), 2.95 (d, J=6.8 Hz, 2H), 1.24-1.07 (m, 1H), 1.01-0.94 (m, 2H), 0.88-0.79 (m, 2H), 0.65-0.51 (m, 2H), 0.34-0.19 (m, 2H). LCMS: M+1=371.0.

EXAMPLE 17

2-(2-(((8-chloro-3-(cyclopropylmethyl)-[1,2,4]triazolo[4,3-a]pyridin-7-yl)amino)methyl)cyclopropyl)benzonitrile. A mixture of 8-chloro-3-(cyclopropyl methyl)-7-iodo-[1,2,4]triazolo[4,3-a]pyridine (60 mg, 0.180 mmol), 2-(2-(aminomethyl)cyclopropyl)benzonitrile (31.0 mg, 0.180 mmol) was reacted in a manner similar to Example 1 to give 2-(2-(((8-chloro-3-(cyclopropylmethyl)-[1,2,4]triazolo[4,3-a]pyridin-7-yl)amino)methyl)cyclopropyl)benzonitrile (24 mg, 32.5%) as a film. $^1$H NMR (400 MHz, METHANOL-d$_4$) δ 8.15 (d, J=7.5 Hz, 1H), 7.62 (dd, J=7.8, 1.0 Hz, 1H), 7.53 (td, J=7.8, 1.3 Hz, 1H), 7.29 (td, J=7.7, 1.0 Hz, 1H), 7.11 (d, J=8.0 Hz, 1H), 6.97 (d, J=7.8 Hz, 1H), 3.65 (dd, J=14.6, 6.0 Hz, 1H), 3.51 (dd, J=14.6, 6.5 Hz, 1H), 2.98 (d, J=6.8 Hz, 2H), 2.28-2.20 (m, 1H), 1.55 (ddd, J=8.7, 6.1, 4.8 Hz, 1H), 1.26-1.08 (m, 3H), 0.65-0.54 (m, 2H), 0.36-0.25 (m, 2H). LCMS: M+1=378.0.

EXAMPLE 18

8-Chloro-3-(cyclopropylmethyl)-N-((2-(pyridin-4-yl)cyclopropyl)methyl)-[1,2,4]triazolo[4,3-a]pyridin-7-amine. A mixture of 8-chloro-3-(cyclopropylmethyl)-7-iodo-[1,2,4]triazolo[4,3-a]pyridine (50 mg, 0.150 mmol) and (2-(pyridin-4-yl)cyclopropyl)methanamine (26.7 mg, 0.180 mmol) was reacted in a manner similar to Example 1 to give 8-chloro-3-(cyclopropylmethyl)-N-((2-(pyridin-4-yl)cyclopropyl)methyl)-[1,2,4]triazolo[4,3-a]pyridin-7-amine (25.7 mg, 47.5%). $^1$H NMR (500 MHz, DMSO-d$_6$) δ 8.35 (d, J=6.1 Hz, 2H), 8.23 (d, J=7.6 Hz, 1H), 7.06 (d, J=6.1 Hz, 2H), 6.90 (d, J=7.6 Hz, 1H), 6.42 (t, J=6.1 Hz, 1H), 2.95 (d, J=6.7 Hz, 2H), 1.95 (dd, J=8.7, 4.4 Hz, 1H), 1.48 (br. s., 1H), 1.19-1.09 (m, 2H), 1.09-1.00 (m, 1H), 0.50 (d, J=6.4 Hz, 2H), 0.25 (d, J=4.6 Hz, 2H). LCMS: M+1=354.2.

EXAMPLE 19

8-Chloro-3-(cyclopropylmethyl)-N-((2-(pyridin-3-yl)cyclopropyl)methyl)-1,2,41-triazolo[4,3-a]pyridin-7-amine. A mixture of 8-chloro-3-(cyclopropylmethyl)-7-iodo-[1,2,4]triazolo[4,3-a]pyridine (15 mg, 0.045 mmol) and (2-(pyridin-3-yl)cyclopropyl)methanamine, HCl (9.97 mg, 0.054 mmol) was reacted in a manner similar to Example 1 to give 8-chloro-3-(cyclopropylmethyl)-N-((2-(pyridin-3-yl)cyclopropyl)methyl)-[1,2,4]triazolo[4,3-a]pyridin-7-amine (5.5 mg, 33.9%). $^1$H NMR (500 MHz, DMSO-d$_6$) δ 8.37 (d, J=1.8 Hz, 1H), 8.32 (d, J=3.7 Hz, 1H), 8.22 (d, J=7.6 Hz, 1H), 7.39 (d, J=7.9 Hz, 1H), 7.24 (dd, J=7.9, 4.9 Hz, 1H), 6.91 (d, J=7.6 Hz, 1H), 6.43 (t, J=6.4 Hz, 1H), 2.94 (d, J=6.7 Hz, 3H), 2.01-1.94 (m, 1H), 1.46-1.35 (m, 1H), 1.18-1.09 (m, 1H), 1.09-0.97 (m, 2H), 0.54-0.44 (m, 2H), 0.28-0.18 (m, 2H). LCMS: M+1=254.2.

EXAMPLE 20

3-(Cyclopropylmethyl)-N-(((1S,2S)-2-(4-fluorophenyl)cyclopropyl)methyl)-8-(trifluoromethyl)-[1,2,4]triazolo[4,3-a]pyridin-7-amine Step 1: 2-chloro-N-(((1S,2S)-2-(4-fluorophenyl)cyclopropyl)methyl)-3-(trifluoromethyl)pyridin-4-amine. A mixture of ((1S,2S)-2-(4-fluorophenyl)cyclopropyl)methanamine, HCl (1.524 g, 7.56 mmol), 2,4-dichloro-3-(trifluoromethyl)pyridine (1.36 g, 6.30 mmol) and TEA (1.141 mL, 8.19 mmol) in acetonitrile (15 mL) was heated to reflux stirring under nitrogen for 6 h. The reaction mixture was concentrated and the residue was purified by silica gel chromatography using 0-30% EtOAc/hexane as the eluent to give 2-chloro-N-(((1S,2S)-2-(4-fluorophenyl)cyclopropyl)methyl)-3-(trifluoromethyl)pyridin-4-amine as a white solid (1.26 g, 55% yield). $^1$H NMR (400 MHz, CHLOROFORM-d) δ 8.06 (d, J=6.0 Hz, 1H), 7.11-6.94 (m, 4H), 6.52 (d, J=6.0 Hz, 1H), 5.60 (br. s., 1H), 3.33-3.14 (m, 2H), 1.91 (dt, J=9.1, 4.9 Hz, 1H), 1.45-1.35 (m, 1H), 1.08 (dt, J=8.3, 5.4 Hz, 1H), 1.00 (dt, J=9.0, 5.4 Hz, 1H).

Step 2: N-(((1S,2S)-2-(4-fluorophenyl)cyclopropyl)methyl)-2-hydrazinyl-3-(trifluoromethyl)pyridin-4-amine. A mixture of 2-chloro-N-(((1S,2S)-2-(4-fluorophenyl)cyclopropyl)methyl)-3-(trifluoromethyl)pyridin-4-amine (0.7 g, 2.031 mmol) and hydrazine monohydrate (2.033 g, 40.6 mmol) in dioxane (8 mL) was heated to reflux under nitrogen for 16 h. The reaction mixture was diluted with EtOAc and extracted with aqueous sodium bicarbonate. The aqueous layer was extracted with EtOAc (2×5 mL). The combined organic layers were washed with aqueous sodium bicarbonate (10 mL) and brine (10 mL), dried over magnesium sulfate, filtered and concentrated under vacuum to give N-(((1S,2S)-2-(4-fluorophenyl)cyclopropyl)methyl)-2-hydrazinyl-3-(trifluoromethyl)pyridin-4-amine (0.7 g, 65%) which was used for the next step without purification.

Step 3: 2-Cyclopropyl-N'-(4-((((1S,2S)-2-(4-fluorophenyl)-cyclopropyl)methyl)amino)-3-(trifluoromethyl)pyridin-2-yl)acetohydrazide. A solution of thionyl chloride (0.713 mL, 8.23 mmol) and 2-cyclopropylacetic acid (0.247 g, 2.468 mmol) in methylene chloride (10 mL) was heated to reflux for 30 min. The solution was cooled and concentrated. The residue was dissolved in EtOAc (10 mL) and added to a stirred mixture of N-(((1S,2S)-2-(4-fluorophenyl)cyclopropyl)methyl)-2-hydrazinyl-3-(trifluoromethyl)pyridin-4-amine (0.56 g, 1.646 mmol) in EtOAc (10 mL), THF (10 mL), and sat'd Na$_2$CO$_3$ (10 mL). The mixture was stirred for 1 h. The reaction was diluted with EtOAc. The organic layer was separated, washed with aqueous sodium bicarbonate, washed with brine, dried over MgSO$_4$, and concentrated to give the crude product. The crude product was purified by silica gel chromatography to give 2-cyclopropyl-N'-(4-((((1S,2S)-2-(4-fluorophenyl)-cyclopropyl)methyl)amino)-3-(trifluoromethyl)pyridin-2-yl)acetohydrazide (360 mg, 49%) as a light yellow gum. $^1$H NMR (400 MHz, CHLOROFORM-d) δ 7.90 (d, J=6.0 Hz, 1H), 7.74 (br. s., 1H), 7.09-6.86 (m, 4H), 6.19 (d, J=6.0 Hz, 1H), 5.40-5.16 (m, 1H), 3.34-3.09 (m, 2H), 2.29 (d, J=7.0 Hz, 3H), 1.88 (dt, J=9.1, 4.9 Hz, 2H), 1.44-1.30 (m, 1H), 1.13-1.02 (m, 2H), 1.01-0.93 (m, 1H), 0.72-0.55 (m, 2H), 0.27 (d, J=5.8 Hz, 2H). LCMS M+1=423.2.

Step 4: 3-(cyclopropylmethyl)-N-(((1S,2S)-2-(4-fluorophenyl)cyclopropyl)methyl)-8-(trifluoromethyl)-[1,2,4]triazolo[4,3-a]pyridin-7-amine. To a mixture of 2-cyclopropyl-N'-(4-((((1S,2S)-2-(4-fluorophenyl)cyclopropyl)methyl)amino)-3-(trifluoromethyl)pyridin-2-yl)acetohydrazide (0.06 g, 0.142 mmol) in THF (4 mL) was added Burgess reagent (0.068 g, 0.284 mmol) and the resulting mixture was refluxed stirring for 6 hours. The reaction mixture diluted with EtOAc and extracted with aqueous sodium bicarbonate. The aqueous layer was extracted with EtOAc (3×10 mL). The combined organic layers were washed with aqueous sodium bicarbonate (2×10 mL) and brine (10 mL), dried over magnesium sulfate, filtered and concentrated under vacuum. The residue was purified by silica gel chromatography to give 3-(cyclopropylmethyl)-N-(((1S,2S)-2-(4-fluorophenyl)cyclopropyl)methyl)-8-(trifluoromethyl)-[1,2,4]triazolo[4,3-a]pyridin-7-amine as a white solid (0.045 g, 74% yield). $^1$H NMR (400 MHz, CHLOROFORM-d) δ 7.98 (d, J=7.5 Hz, 1H), 7.09-7.01 (m, 2H), 7.00-6.92 (m, 2H), 6.64 (d, J=7.8 Hz, 1H), 5.49 (d, J=4.0 Hz, 1H), 3.39 (tdd, J=19.0, 12.8, 5.6 Hz, 2H), 3.01 (d, J=6.8 Hz, 2H), 1.92 (dt, J=9.1, 4.9 Hz, 1H), 1.46-1.34 (m, 1H), 1.19-0.94 (m, 3H), 0.65-0.54 (m, 2H), 0.37-0.27 (m, 2H). LCMS M+1=405.05.

EXAMPLE 21

Step 1: 3,3,3-trifluoro-N'-(4-((((1S,2S)-2-(4-fluorophenyl)cyclopropyl)methyl)amino)-3-(trifluoromethyl)pyridin-2-yl)propanehydrazide. A mixture of N-(((1S,2S)-2-(4-fluorophenyl)cyclopropyl)methyl)-2-hydrazinyl-3-(trifluoromethyl)pyridin-4-amine (0.38 g, 1.117 mmol) in EtOAc (3 mL) and THF (3 mL) and sat'd aqueous sodium carbonate (3 mL) was stirred as 3,3,3-trifluoropropanoyl chloride (0.213 g, 1.452 mmol) was added slowly. The mixture was stirred for 10 min. The reaction was diluted with EtOAc, washed with aqueous sodium bicarbonate, dried with brine, and concentrated. The crude product was purified by silica gel chromatography using 0-100% ethyl acetate/hexane as the eluent to give 3,3,3-trifluoro-N'-(4-((((1S,2S)-2-(4-fluorophenyl)cyclopropyl)methyl)amino)-3-(trifluoromethyl)pyridin-2-yl)propanehydrazide as an off-white solid (0.4 g, 71.6% yield). $^1$H NMR (400 MHz, CHLOROFORM-d) d 7.87 (d, J=6.3 Hz, 1H), 7.08-6.92 (m, 4H), 6.23 (d, J=6.3 Hz, 1H), 5.35 (d, J=3.8 Hz, 1H), 3.35-3.12 (m, 4H), 1.89 (dt, J=9.1, 4.9 Hz, 1H), 1.44-1.31 (m, 1H), 1.07 (dt, J=8.4, 5.5 Hz, 1H), 0.98 (dt, J=8.9, 5.5 Hz, 1H). LCMS M+1=451.1.

Step 2: N-(((1S,2S)-2-(4-Fluorophenyl)cyclopropyl)methyl)-3-(2,2,2-trifluoroethyl)-8-(trifluoromethyl)-[1,2,4]triazolo[4,3-a]pyridin-7-amine. Burgess reagent (0.370 g, 1.554 mmol) was added to a solution of 3,3,3-trifluoro-N'-(4-((((1S,2S)-2-(4-fluorophenyl)cyclopropyl)methyl)amino)-3-(trifluoromethyl)pyridin-2-yl)propanehydrazide (0.35 g, 0.777 mmol) in THF (10 mL). The resulting mixture was stirred in a sealed microwave tube at 70° C. under nitrogen for 6 h. The reaction mixture was diluted with EtOAc and washed with aqueous sodium bicarbonate. The aqueous layer was extracted with EtOAc (3×10 mL). The combined organic layers were washed with aqueous sodium bicarbonate (20 mL), dried with brine (20 mL), and concentrated under vacuum. The crude material was purified by preparative HPLC on a Phenomenex-Luna 30×100 mm S10 Axia column, using 10-90% MeOH/water containing 0.1% to give 170 mg of product. This material was further purified by silica gel chromatography using 0-5% MeOH/EtOAc as the eluent to give N-(((1S,2S)-2-(4-fluorophenyl)cyclopropyl)methyl)-3-(2,2,2-trifluoroethyl)-8-(trifluoromethyl)-[1,2,4]triazolo[4,3-a]pyridin-7-amine as a white solid (140 mg, 40.8% yield). $^1$H NMR (400 MHz, METHANOL-d4) δ 8.37 (d, J=7.8 Hz, 1H), 7.12-7.00 (m, 3H), 6.97-6.82 (m, 2H), 4.19 (d, J=10.0 Hz, 2H), 3.48 (d, J=6.5 Hz, 2H), 2.06-1.86 (m, 1H), 1.49-1.31 (m, 1H), 1.00 (ddd, J=8.4, 5.5, 3.1 Hz, 2H). LCMS: M+1=433.3.

EXAMPLE 22

3-(Cyclopropylmethyl)-N-(((1R,2R)-2-(4-fluorophenyl)cyclopropyl)methyl)-8-(trifluoromethyl)-[1,2,4]triazolo[4,3-a]pyridin-7-amine. ((1R,2R)-2-(4-Fluorophenyl)cyclopropyl)methanamine, HCl (13.17 mg, 0.065 mmol) was reacted in a manner similar to Example 21 to give 3-(cyclopropylmethyl)-N-(((1R,2R)-2-(4-fluorophenyl)cyclopropyl)methyl)-8-(trifluoromethyl)-[1,2,4]triazolo[4,3-a]pyridin-7-amine as a film (1.0 mg, 4%). $^1$H NMR (400 MHz, METHANOL-d4) δ 8.28 (d, J=8.0 Hz, 1H), 7.12-7.04 (m, 2H), 7.00-6.91 (m, 3H), 3.49 (dd, J=6.5, 2.0 Hz, 2H), 2.99 (d, J=7.0 Hz, 2H), 2.02-1.93 (m, 1H), 1.48-1.34 (m, 1H), 1.24-1.13 (m, 1H), 1.02 (ddd, J=8.1, 6.0, 1.8 Hz, 2H), 0.65-0.55 (m, 2H), 0.38-0.26 (m, 2H). LCMS: M+1=405.2.

EXAMPLE 23

Trans-N-((2-(4-fluorophenyl)cyclopropyl)methyl)-N-methyl-3-(2,2,2-trifluoro ethyl)-8-(trifluoromethyl)-[1,2,4]triazolo[4,3-a]pyridin-7-amine Step 1: Trans-2-chloro-N-((2-(4-fluorophenyl)cyclopropyl)methyl)-3-(trifluoromethyl)pyridin-4-amine. A mixture of racemic trans-(2-(4-fluorophenyl)cyclopropyl)methanamine, HCl (1.681 g, 8.33 mmol), 2,4-dichloro-3-(trifluoromethyl)pyridine (1.5 g, 6.94 mmol) and TEA (1.258 mL, 9.03 mmol) in acetonitrile (15 mL) was heated to reflux under nitrogen for 2 h. The reaction mixture was concentrated. The residue suspended in dichloromethane and filtered. The filtrate was concentrated and purified by silica gel chromatography, using 0-30% EtOAc/hexane as the eluent, to give 2-chloro-N-((2-(4-fluorophenyl)cyclopropyl)methyl)-3-(trifluoromethyl)pyridin-4-amine (1.127 g, 47.1% yield) as a white solid. ¹H NMR (400 MHz, CHLOROFORM-d) δ 8.06 (d, J=6.0 Hz, 1H), 7.10-6.92 (m, 4H), 6.52 (d, J=6.0 Hz, 1H), 5.67-5.51 (m, 1H), 3.34-3.13 (m, 2H), 1.91 (dt, J=9.1, 4.9 Hz, 1H), 1.44-1.33 (m, 1H), 1.08 (dt, J=8.4, 5.5 Hz, 1H), 0.99 (dt, J=8.9, 5.3 Hz, 1H).

Step 2: Trans-2-chloro-N-((2-(4-fluorophenyl)cyclopropyl)methyl)-N-methyl-3-(trifluoromethyl)pyridin-4-amine. To a solution of trans-2-chloro-N-((2-(4-fluorophenyl)cyclopropyl)methyl)-3-(trifluoromethyl)pyridin-4-amine (1.2 g, 3.48 mmol) in DMF (5 mL) was added 60% sodium hydride in mineral oil (0.153 g, 3.83 mmol) at 0° C. The resulting mixture was stirred at 0° C. under nitrogen for 10 min. Iodomethane (0.022 mL, 0.346 mmol) was added at 0° C. The reaction mixture was stirred at 0° C. for 10 min and then at rt for 30 min. The reaction mixture was poured into ice water and the resulting suspension was extracted with EtOAc (3×20 mL). The combined organic layers were washed with aqueous sodium bicarbonate (2×20 mL) and brine (20 mL), dried over magnesium sulfate, filtered and concentrated under vacuum to give trans-2-chloro-N-((2-(4-fluorophenyl)cyclopropyl)methyl)-N-methyl-3-(trifluoromethyl)pyridin-4-amine (1.2 g, 96% yield) as a yellowish oil, which was used for the next step reaction without further purification. ¹H NMR (400 MHz, CHLOROFORM-d) δ 8.07 (d, J=5.8 Hz, 1H), 7.01-6.94 (m, 4H), 6.80 (d, J=6.0 Hz, 1H), 3.38 (dd, J=14.1, 6.0 Hz, 1H), 3.18 (dd, J=14.1, 7.3 Hz, 1H), 3.06-3.00 (m, 3H), 1.75-1.63 (m, 1H), 1.24 (br. s., 1H), 1.03 (dt, J=8.5, 5.3 Hz, 1H), 0.90-0.84 (m, 1H). LCMS: M+1=359.17.

Step 3: Trans-N-((2-(4-fluorophenyl)cyclopropyl)methyl)-2-hydrazinyl-N-methyl-3-(trifluoromethyl)pyridin-4-amine. A mixture of trans 2-chloro-N-((2-(4-fluorophenyl)cyclopropyl)methyl)-N-methyl-3-(trifluoromethyl)pyridin-4-amine (1.2 g, 3.34 mmol) and hydrazine hydrate (3.32 mL, 66.9 mmol) in dioxane (20 mL) was heated to reflux under nitrogen for 6 h. The reaction mixture was concentrated. The reaction mixture was diluted with EtOAc and washed with aqueous sodium bicarbonate. The aqueous layer was extracted with EtOAc (3×20 mL). The combined organic layers were washed with aqueous sodium bicarbonate (2×20 mL) and brine (20 mL), dried over magnesium sulfate, and concentrated to give trans-N-((2-(4-fluorophenyl)cyclopropyl)methyl)-2-hydrazinyl-N-methyl-3-(trifluoromethyl)pyridin-4-amine (1.1 g, 80% yield), which was used for the next reaction without further purification.

Step 4: Trans-3,3,3-trifluoro-N'-(4-(((2-(4-fluorophenyl)cyclopropyl)methyl)(methyl)amino)-3-(trifluoromethyl)pyridin-2-yl)propanehydrazide. To a mixture of trans-N-((2-(4-fluorophenyl)cyclopropyl)methyl)-2-hydrazinyl-N-methyl-3-(trifluoromethyl)pyridin-4-amine (0.5 g, 1.411 mmol) in EtOAc (6 mL), THF (6 mL) and 2.0 M of aqueous sodium carbonate (3.53 mL, 7.06 mmol) was added 3,3,3-trifluoropropionyl chloride (0.248 g, 1.693 mmol) dropwise at rt. The resulting mixture was stirred at under nitrogen for 10 min. The reaction mixture was partitioned between EtOAc/aqueous sodium bicarbonate. The aqueous layer was extracted with EtOAc (3×20 mL). The combined organic layers were washed with aqueous sodium bicarbonate (2×20 mL) and brine (20 mL), dried over magnesium sulfate, filtered, and concentrated. The residue was purified by silica gel chromatography using 0-30% EtOAc/hexane as the eluent to give trans-3,3,3-trifluoro-N'-(4-(((2-(4-fluorophenyl)cyclopropyl)methyl)(methyl)amino)-3-(trifluoromethyl)pyridin-2-yl)propanehydrazide (0.46 g, 66.7% yield) as a white solid. ¹H NMR (500 MHz, METHANOL-d4) δ 7.88 (d, J=6.0 Hz, 1H), 7.08-7.01 (m, 2H), 6.99-6.91 (m, 2H), 6.58 (d, J=6.1 Hz, 1H), 3.41 (dd, J=14.0, 5.6 Hz, 1H), 3.36-3.24 (m, 2H), 3.13 (dd, J=14.0, 7.6 Hz, 1H), 1.81-1.71 (m, 1H), 1.32-1.21 (m, 1H), 0.99 (dt, J=8.6, 5.2 Hz, 1H), 0.87 (dt, J=8.8, 5.4 Hz, 1H). LCMS: M+1=465.13.

Step 5: Trans-N-((2-(4-fluorophenyl)cyclopropyl)methyl)-N-methyl-3-(2,2,2-trifluoroethyl)-8-(trifluoromethyl)-[1,2,4]triazolo[4,3-a]pyridin-7-amine. A mixture of 3,3,3-trifluoro-N'-(4-(((2-(4-fluorophenyl)cyclopropyl)methyl)(methyl)amino)-3-(trifluoromethyl)pyridin-2-yl)propanehydrazide (0.5 g, 1.077 mmol) and Burgess reagent (0.513 g, 2.153 mmol) in THF (10 mL) was heated to reflux stirring for 90 min. The reaction mixture was diluted with EtOAc and washed with aqueous sodium bicarbonate. The aqueous layer was extracted with EtOAc (3×20 mL). The combined organic layers were washed with aqueous sodium bicarbonate (2×20 mL), dried with brine (20 mL), dried over magnesium sulfate, and concentrated. The residue was purified by silica gel chromatography using 0-100% EtOAc/hexane as the eluent to give N-((2-(4-fluorophenyl)cyclopropyl)methyl)-N-methyl-3-(2,2,2-trifluoroethyl)-8-(trifluoromethyl)-[1,2,4]triazolo[4,3-a]pyridin-7-amine as a yellow solid (0.14 g, 26.5%). ¹H NMR (400 MHz, CHLOROFORM-d) δ 7.91 (d, J=7.8 Hz, 1H), 7.03-6.91 (m, 4H), 6.83 (d, J=7.8 Hz, 1H), 4.02 (q, J=9.8 Hz, 2H), 3.48 (dd, J=14.1, 6.0 Hz, 1H), 3.33 (dd, J=14.1, 7.3 Hz, 1H), 3.16 (s, 3H), 1.77 (dd, J=9.0, 4.8 Hz, 1H), 1.34-1.23 (m, 1H), 1.05 (dt, J=8.5, 5.4 Hz, 1H), 0.91 (dt, J=8.8, 5.5 Hz, 1H). LCMS: M+1=447.12.

EXAMPLE 24

Trans-3-(cyclopropylmethyl)-N-((2-(4-fluorophenyl)cyclopropyl)methyl)-N-methyl-8-(trifluoromethyl)-[1,2,4]triazolo[4,3-a]pyridin-7-amine Step 1: Trans-2-cyclopropyl-N'-(4-(((2-(4-fluorophenyl)cyclopropyl)methyl)(methyl)amino)-3-(trifluoromethyl)pyridin-2-yl)acetohydrazide. Trans-2-cyclopropyl-N'-(4-(((2-(4-fluorophenyl)cyclopropyl)methyl)(methyl)amino)-3-(trifluoromethyl)pyridin-2-yl)acetohydrazide was obtained in a manner similar to Example 23, Step 4 (0.4 g, 48.1% yield).

Step 2: Trans-3-(cyclopropylmethyl)-N-((2-(4-fluorophenyl)cyclopropyl)methyl)-N-methyl-8-(trifluoromethyl)-[1,2,4]triazolo[4,3-a]pyridin-7-amine. Trans-3-(cyclopropylmethyl)-N-((2-(4-fluorophenyl)cyclopropyl)methyl)-N-methyl-8-(trifluoromethyl)-[1,2,4]triazolo[4,3-a]pyridin-7-amine was obtained in a manner similar to Example 23, Step 5, as a yellow solid (0.3 g, 59.9%). ¹H NMR (400 MHz, CHLOROFORM-d) δ 7.86 (d, J=7.8 Hz, 1H), 7.02-6.92 (m, 4H), 6.73 (d, J=7.8 Hz, 1H), 3.44 (dd, J=13.9, 6.1 Hz, 1H), 3.28 (dd, J=14.1, 7.0 Hz, 1H), 3.11 (s, 3H), 3.02 (d, J=6.8 Hz, 2H), 1.79-1.74 (m, 1H), 1.32-1.21 (m, 1H), 1.19-1.08 (m, 1H), 1.03 (dt, J=8.5, 5.3 Hz, 1H), 0.89 (dt, J=8.8, 5.5 Hz, 1H), 0.66-0.55 (m, 2H), 0.37-0.24 (m, 2H). LCMS: M+1=419.19.

EXAMPLE 25

N-((2-(4-Fluorophenyl)cyclopropyl)methyl)-3-(2,2,2-trifluoroethyl)-8-(trifluoromethyl)imidazo[1,2-a]pyridin-7-amine. A mixture of 7-chloro-3-(2,2,2-trifluoroethyl)-8-(trifluoromethyl)imidazo[1,2-a]pyridine (100 mg, 0.330 mmol), (2-(4-fluorophenyl)cyclopropyl)methanamine, HCl (83 mg, 0.413 mmol), and Hunig's base (173 μl, 0.991 mmol) in acetonitrile (3305 μl) was heated to 160° C. in a sealed vial for 16 hr. The mixture was diluted with dichloromethane, washed with water, dried with brine, and concentrated. The crude material was purified by silica gel chromatography using 0-40% EtOAc/hexanes as the eluent to give N-((2-(4-fluorophenyl)cyclopropyl)methyl)-3-(2,2,2-trifluoroethyl)-8-(trifluoromethyl)imidazo[1,2-a]pyridin-7-amine as a yellow oil (29 mg, 19.5%). $^1$H NMR (400 MHz, CHLOROFORM-d) δ ppm 7.90 (d, J=7.8 Hz, 1H), 7.48 (s, 1H), 7.08-7.02 (m, 2H), 7.01-6.94 (m, 2H), 6.57 (d, J=7.8 Hz, 1H), 5.45-5.30 (m, J=4.8 Hz, 1H), 3.66 (q, J=9.9 Hz, 2H), 3.44-3.24 (m, 2H), 1.97-1.86 (m, 1H), 1.46-1.33 (m, 1H), 1.08 (dt, J=8.3, 5.4 Hz, 1H), 1.00 (dt, J=8.9, 5.3 Hz, 1H). Mass found 432 [M+H]+.

EXAMPLE 26

7-(((2-(3-Fluorophenyl)cyclopropyl)methyl)amino)-3-(2,2,2-trifluoroethyl)imidazo[1,2-a]pyridine-8-carbonitrile. A mixture of 7-chloro-3-(2,2,2-trifluoroethyl)imidazo[1,2-a]pyridine-8-carbonitrile (30 mg, 0.116 mmol), (2-(3-fluorophenyl)cyclopropyl)methanamine, HCl (35.0 mg, 0.173 mmol) and Hunig's base (60.5 µl, 0.347 mmol) in DMF (1.15 mL) was heated to 120° C. in a sealed vial for 16 hr. The crude material was purified via preparative LC/MS on a Waters XBridge C18, 19×200 mm, 5-mm column using 40-100% acetonitrile:water with 20-mM ammonium acetate as the eluent to give 7-(((2-(3-fluoro phenyl)cyclopropyl)methyl) amino)-3-(2,2,2-trifluoroethyl)imidazo[1,2-a]pyridine-8-carbonitrile (9.7 mg, 22%). $^1$H NMR (500 MHz, DMSO-d6) δ ppm 8.40 (d, J=7.6 Hz, 1H), 7.37 (t, J=6.0 Hz, 1H), 7.30-7.22 (m, 2H), 6.96-6.90 (m, 2H), 6.90-6.86 (m, J=10.7, 1.8 Hz, 1H), 6.82 (d, J=7.6 Hz, 1H), 4.08 (q, J=10.7 Hz, 2H), 3.53-3.46 (m, 1H), 3.45-3.38 (m, 1H), 2.02-1.96 (m, 1H), 1.49-1.40 (m, 1H), 1.05 (dt, J=8.9, 5.2 Hz, 1H), 1.02-0.97 (m, 1H). Mass found 389 [M+H]+.

EXAMPLE 27

7-(((2-(2-Fluoro-6-methoxyphenyl)cyclopropyl)methyl) amino)-3-(2,2,2-trifluoroethyl)imidazo[1,2-a]pyridine-8-carbonitrile. (2-(2-Fluoro-6-methoxyphenyl)cyclopropyl) methanamine, HCl, was reacted under conditions similar to Example 26 to give 7-(((2-(2-Fluoro-6-methoxyphenyl)cyclopropyl)methyl)amino)-3-(2,2,2-trifluoroethyl)imidazo[1,2-a]pyridine-8-carbonitrile (7.3 mg, 15%). $^1$H NMR (500 MHz, DMSO-d$_6$) δ 8.42 (d, J=7.9 Hz, 1H), 7.27 (s, 1H), 7.24 (t, J=6.0 Hz, 1H), 7.19-7.12 (m, 1H), 6.81 (d, J=7.9 Hz, 1H), 6.78 (d, J=8.2 Hz, 1H), 6.69 (dd, J=10.2, 8.7 Hz, 1H), 4.08 (q, J=10.9 Hz, 2H), 3.74 (s, 3H), 3.58-3.50 (m, 1H), 1.83-1.77 (m, 1H), 1.58 (dq, J=12.9, 6.3 Hz, 1H), 1.05 (dt, J=8.4, 5.1 Hz, 1H), 0.93 (dt, J=9.3, 4.8 Hz, 1H). Mass found 419 [M+H]+.

EXAMPLE 28

3-(2,2,2-Trifluoroethyl)-7-(((2-(2-(trifluoromethoxy)phenyl)cyclopropyl)methyl)amino)imidazo[1,2-a]pyridine-8-carbonitrile. (2-(2-(Trifluoromethoxy)phenyl)cyclopropyl) methanamine, HCl, was reacted under conditions similar to Example 26 to give 3-(2,2,2-Trifluoroethyl)-7-(((2-(2-(trifluoromethoxy)phenyl)cyclopropyl)methyl)amino)imidazo [1,2-a]pyridine-8-carbonitrile (7.6 mg, 14.5%). $^1$H NMR (500 MHz, DMSO-d$_6$) δ 8.40 (d, J=7.9 Hz, 1H), 7.33 (t, J=6.0 Hz, 1H), 7.27 (d, J=4.6 Hz, 4H), 7.05 (dd, J=7.6, 2.1 Hz, 1H), 6.81 (d, J=7.9 Hz, 1H), 4.08 (q, J=11.0 Hz, 2H), 3.58-3.50 (m, 1H), 3.50-3.43 (m, 1H), 2.16-2.05 (m, 1H), 1.59-1.45 (m, 1H), 1.11 (dt, J=8.9, 5.2 Hz, 1H), 1.04-0.95 (m, 1H). Mass found 455 [M+H]+.

EXAMPLE 29

7-(((2-(2-Methoxyphenyl)cyclopropyl)methyl)amino)-3-(2,2,2-trifluoroethyl)imidazo[1,2-a]pyridine-8-carbonitrile. (2-(2-Methoxyphenyl)cyclopropyl)methanamine, HCl, was reacted under conditions similar to Example 26 to give 7-(((2-(2-Methoxyphenyl)cyclopropyl)methyl)amino)-3-(2,2,2-trifluoroethyl)imidazo[1,2-a]pyridine-8-carbonitrile (10.6 mg, 31%). $^1$H NMR (500 MHz, DMSO-d$_6$) δ 8.40 (d, J=7.9 Hz, 1H), 7.33 (t, J=6.0 Hz, 1H), 7.27 (d, J=4.6 Hz, 4H), 7.05 (dd, J=7.6, 2.1 Hz, 1H), 6.81 (d, J=7.9 Hz, 1H), 4.08 (q, J=11.0 Hz, 2H), 3.58-3.50 (m, 1H), 3.50-3.43 (m, 1H), 2.16-2.05 (m, 1H), 1.59-1.45 (m, 1H), 1.11 (dt, J=8.9, 5.2 Hz, 1H), 1.04-0.95 (m, 1H). Mass found 401 [M+H]+.

EXAMPLE 30

7-(((2-(4-Fluorophenyl)cyclopropyl)methyl)amino)-3-(2,2,2-trifluoroethyl)imidazo[1,2-a]pyridine-8-carbonitrile. (2-(4-Fluorophenyl)cyclopropyl)methanamine, HCl, was reacted under conditions similar to Example 26 to give 7-(((2-(4-Fluorophenyl)cyclopropyl)methyl)amino)-3-(2,2,2-trifluoroethyl)imidazo[1,2-a]pyridine-8-carbonitrile (8.1 mg, 29%). $^1$H NMR (500 MHz, DMSO-d$_6$) δ 8.40 (d, J=7.6 Hz, 1H), 7.39 (t, J=6.0 Hz, 1H), 7.26 (s, 1H), 7.14-7.00 (m, 4H), 6.82 (d, J=7.9 Hz, 1H), 4.08 (q, J=11.0 Hz, 2H), 3.52-3.45 (m, 1H), 3.45-3.38 (m, 1H), 1.96 (dt, J=8.9, 4.7 Hz, 1H), 1.42-1.34 (m, 1H), 1.06-0.97 (m, 1H), 0.96-0.89 (m, 1H). Mass found 389 [M+H]+.

EXAMPLE 31

N-(((1S,2S)-2-(4-Fluorophenyl)cyclopropyl)methyl)-3-(2,2,2-trifluoroethyl)-8-(trifluoromethyl)imidazo[1,2-a]pyridin-7-amine. This compound was obtained from racemic material by chiral HPLC on a ChiralCel OJ-H, 5µ, 4.6×100 mm, column using either 15% heptane/ethanol/0.1% diethylamine as the eluent. $^1$H NMR (400 MHz, CHLOROFORM-d) δ ppm 7.90 (d, J=7.8 Hz, 1H), 7.48 (s, 1H), 7.08-7.02 (m, 2H), 7.01-6.94 (m, 2H), 6.57 (d, J=7.8 Hz, 1H), 5.45-5.30 (m, J=4.8 Hz, 1H), 3.66 (q, J=9.9 Hz, 2H), 3.44-3.24 (m, 2H), 1.97-1.86 (m, 1H), 1.46-1.33 (m, 1H), 1.08 (dt, J=8.3, 5.4 Hz, 1H), 1.00 (dt, J=8.9, 5.3 Hz, 1H). Mass found 432 [M+H]+.

EXAMPLE 32

N-(((1R,2R)-2-(4-Fluorophenyl)cyclopropyl)methyl)-3-(2,2,2-trifluoroethyl)-8-(trifluoromethyl)imidazo[1,2-a]pyridin-7-amine. This compound was obtained from racemic material by chiral HPLC on a ChiralCel OJ-H, 5µ, 4.6×100 mm, column using 15% heptane/ethanol/0.1% diethylamine as the eluent. $^1$H NMR of the product was consistent with desired. $^1$H NMR (400 MHz, CHLOROFORM-d) δ ppm 7.90 (d, J=7.8 Hz, 1H), 7.48 (s, 1H), 7.08-7.02 (m, 2H), 7.01-6.94 (m, 2H), 6.57 (d, J=7.8 Hz, 1H), 5.45-5.30 (m, J=4.8 Hz, 1H), 3.66 (q, J=9.9 Hz, 2H), 3.44-3.24 (m, 2H), 1.97-1.86 (m, 1H), 1.46-1.33 (m, 1H), 1.08 (dt, J=8.3, 5.4 Hz, 1H), 1.00 (dt, J=8.9, 5.3 Hz, 1H). Mass found 432 [M+H]+.

EXAMPLE 33

8-Chloro-3-(cyclopropylmethyl)-N-(((1S,2S)-2-(2-fluoro-6-methoxyphenyl)cyclopropyl)methyl)-[1,2,4]triazolo[4,3-a]pyridin-7-amine. Racemic 8-Chloro-3-(cyclopropylmethyl)-N-((-2-(2-fluoro-6-methoxyphenyl)cyclopropyl) methyl)-[1,2,4]triazolo[4,3-a]pyridin-7-amine was prepared in a manner similar to Example 1 (180 mg, 99% yield) as off-white solid. LCMS: M+1=401.15. The racemic material was resolved by SCF HPLC on a ChiralPak AD-H, 30×250 mm, 5 µm, column; using 30% MeOH containing 0.1% DEA)/80% CO$_2$ as the mobile phase at 120 bar, 35° C., and 70 mL/min, (82 mg). ¹H NMR (500 MHz, METHANOL-d4) δ 8.16 (d, J=7.6 Hz, 1H), 7.14 (td, J=8.2, 6.8 Hz, 1H), 6.91 (d, J=7.6 Hz, 1H), 6.74 (d, J=8.2 Hz, 1H), 6.66-6.57 (m, 1H), 3.84 (s, 3H), 3.67 (dd, J=13.5, 5.6 Hz, 1H), 3.22 (dd, J=13.4, 7.8 Hz, 1H), 2.99 (d, J=6.9 Hz, 2H), 1.80-1.64 (m, 1H), 1.56-1.43 (m, 1H), 1.27-1.17 (m, 1H), 1.17-1.07 (m, 1H), 1.02-0.90 (m, 1H), 0.67-0.54 (m, 2H), 0.39-0.21 (m, 2H). LCMS: M+1=401.2.

EXAMPLE 34

8-Chloro-3-(cyclopropylmethyl)-N-(((1R,2R)-2-(2-fluoro-6-methoxyphenyl)cyclopropyl)methyl)-[1,2,4]triazolo[4,3-a]pyridin-7-amine. Racemic 8-Chloro-3-(cyclopropylmethyl)-N-((-2-(2-fluoro-6-methoxyphenyl)cyclopropyl)methyl)-[1,2,4]triazolo[4,3-a]pyridin-7-amine was prepared in a manner similar to Example 1 (180 mg, 99% yield) as off-white solid. LCMS: M+1=401.15. The racemic material was resolved by SCF HPLC on a ChiralPak AD-H, 30×250 mm, 5 μm, column; using 30% MeOH containing 0.1% DEA)/80% CO₂ as the mobile phase at 120 bar, 35° C., and 70 mL/min, (60 mg). ¹H NMR (500 MHz, METHANOL-d4) δ 8.16 (d, J=7.6 Hz, 1H), 7.23-7.06 (m, 1H), 6.91 (d, J=7.6 Hz, 1H), 6.74 (d, J=8.2 Hz, 1H), 6.62 (dd, J=9.7, 8.9 Hz, 1H), 3.84 (s, 3H), 3.67 (dd, J=13.4, 5.6 Hz, 1H), 3.22 (dd, J=13.5, 7.9 Hz, 1H), 2.99 (d, J=6.9 Hz, 2H), 1.80-1.65 (m, 1H), 1.57-1.44 (m, 1H), 1.27-1.07 (m, 2H), 1.04-0.93 (m, 1H), 0.66-0.52 (m, 2H), 0.33 (d, J=5.8 Hz, 2H). LCMS: M+1=401.2.

EXAMPLE 35

8-Chloro-3-(cyclopropylmethyl)-N-(((1S,2S)-2-(2,3-dihydrobenzofuran-7-yl)cyclopropyl)methyl)-[1,2,4]triazolo[4,3-a]pyridin-7-amine. A mixture of 8-chloro-3-(cyclopropylmethyl)-7-iodo-[1,2,4]triazolo[4,3-a]pyridine (150 mg, 0.450 mmol) and racemic (2-(2,3-dihydrobenzofuran-7-yl)cyclopropyl)methanamine, HCl (122 mg, 0.540 mmol) was reacted in a manner similar to Example 1 to give racemic 8-chloro-3-(cyclopropylmethyl)-N-((2-(2,3-dihydrobenzofuran-7-yl)cyclopropyl)methyl)-[1,2,4]triazolo[4,3-a]pyridin-7-amine (100 mg, 45% yield) as an off-white solid. LCMS: M+1=395.15. The racemic material was resolved by SCF HPLC on a ChiralPak OD-H, 30×250 mm, 5 μm, column; using 25% MeOH containing 0.1% DEA/75% CO₂ as the mobile phase at 150 bar, 35° C., and 70 mL/min, to give 8-chloro-3-(cyclopropylmethyl)-N-(((1S,2S)-2-(2,3-dihydrobenzo furan-7-yl)cyclopropyl)methyl)-[1,2,4]triazolo[4,3-a]pyridin-7-amine (41 mg, 39% yield). ¹H NMR (400 MHz, METHANOL-d4) δ 8.10 (d, J=7.8 Hz, 1H), 6.98 (d, J=7.0 Hz, 1H), 6.84 (d, J=7.5 Hz, 1H), 6.77-6.59 (m, 2H), 4.53 (t, J=8.9 Hz, 2H), 3.64 (dd, J=13.1, 5.5 Hz, 1H), 3.15 (t, J=8.7 Hz, 2H), 3.05 (dd, J=13.1, 8.3 Hz, 1H), 2.95 (d, J=6.8 Hz, 2H), 1.90-1.76 (m, 1H), 1.33-1.13 (m, 2H), 1.12-1.00 (m, 1H), 0.96-0.80 (m, 1H), 0.66-0.51 (m, 2H), 0.31 (q, J=4.9 Hz, 2H) LCMS: M+1=395.15. ee %=93.2%.

EXAMPLE 36

8-Chloro-3-(cyclopropylmethyl)-N-(((1R,2R)-2-(2,3-dihydrobenzofuran-7-yl)cyclopropyl)methyl)-[1,2,4]triazolo[4,3-a]pyridin-7-amine. A mixture of 8-chloro-3-(cyclopropylmethyl)-7-iodo-[1,2,4]triazolo[4,3-a]pyridine (150 mg, 0.450 mmol) and racemic (2-(2,3-dihydrobenzofuran-7-yl)cyclopropyl)methanamine, HCl (122 mg, 0.540 mmol) was reacted in a manner similar to Example 1 to give racemic 8-chloro-3-(cyclopropylmethyl)-N-((2-(2,3-dihydrobenzofuran-7-yl)cyclopropyl)methyl)-[1,2,4]triazolo[4,3-a]pyridin-7-amine (100 mg, 45% yield) as an off-white solid. LCMS: M+1=395.15. The racemic material was resolved by SCF HPLC on a ChiralPak OD-H, 30×250 mm, 5 μm, column; using 25% MeOH containing 0.1% DEA/75% CO₂ as the mobile phase at 150 bar, 35° C., and 70 mL/min, to give 8-chloro-3-(cyclopropylmethyl)-N-(((1R,2R)-2-(2,3-dihydrobenzofuran-7-yl)cyclopropyl)methyl)-[1,2,4]triazolo[4,3-a]pyridin-7-amine (41 mg, 39% yield). ¹H NMR (400 MHz, METHANOL-d4) δ 8.10 (d, J=7.5 Hz, 1H), 6.97 (d, J=6.8 Hz, 1H), 6.83 (d, J=7.5 Hz, 1H), 6.78-6.57 (m, 2H), 4.53 (t, J=8.8 Hz, 2H), 3.64 (dd, J=12.9, 5.4 Hz, 1H), 3.15 (t, J=8.7 Hz, 2H), 3.04 (dd, J=12.9, 8.4 Hz, 1H), 2.95 (d, J=6.8 Hz, 2H), 1.92-1.69 (m, 1H), 1.28-1.13 (m, 2H), 1.10-0.99 (m, 1H), 0.95-0.79 (m, 1H), 0.59 (d, J=7.0 Hz, 2H), 0.38-0.18 (m, 2H). M+1=395.15. ee %=99.9%.

EXAMPLE 37

8-Chloro-3-(cyclopropylmethyl)-N-(((1S,2S)-2-(2-fluorophenyl)cyclopropyl)methyl)-[1,2,4]triazolo[4,3-a]pyridin-7-amine. This compound was obtained from racemic material by SCF HPLC on a ChiralPak AD-H, 30×250 mm, 5 μm, column; using 30% MeOH containing 0.1% DEA)/80% CO₂ as the mobile phase at 120 bar, 35° C., and 70 mL/min, (66 mg, 44.8% yield). ¹H NMR (400 MHz, METHANOL-d4) δ 8.15 (d, J=7.8 Hz, 1H), 7.19-7.09 (m, 1H), 7.06-6.95 (m, 3H), 6.94 (d, J=7.5 Hz, 1H), 3.57-3.40 (m, 2H), 2.98 (d, J=6.8 Hz, 2H), 2.14-2.03 (m, 1H), 1.50-1.37 (m, 1H), 1.25-1.13 (m, 1H), 1.12-0.99 (m, 2H), 0.64-0.55 (m, 2H), 0.36-0.25 (m, 2H). LCMS: M+1=371.15. ee %=99.82%.

EXAMPLE 38

8-Chloro-3-(cyclopropylmethyl)-N-(((1R,2R)-2-(2-fluorophenyl)cyclopropyl)methyl)-[1,2,4]triazolo[4,3-a]pyridin-7-amine. This compound was obtained from racemic material by SCF HPLC on a ChiralPak AD-H, 30×250 mm, 5 μm, column; using 30% MeOH containing 0.1% DEA)/80% CO₂ as the mobile phase at 120 bar, 35° C., and 70 mL/min, (66 mg, 0.169 mmol, 44.8% yield). ¹H NMR (400 MHz, METHANOL-d4) δ 8.16 (d, J=7.5 Hz, 1H), 7.18-7.10 (m, 1H), 7.07-6.96 (m, 3H), 6.95 (d, J=7.5 Hz, 1H), 3.58-3.41 (m, 2H), 2.99 (d, J=7.0 Hz, 2H), 2.15-2.02 (m, 1H), 1.50-1.37 (m, 1H), 1.25-1.16 (m, 1H), 1.11-0.98 (m, 2H), 0.64-0.54 (m, 2H), 0.36-0.27 (m, 2H). LCMS: M+1=371.15. ee %=99.32%.

EXAMPLE 39

3-(Cyclopropylmethyl)-N-(((1S,2S)-2-(4-fluorophenyl)cyclopropyl)methyl)-N-methyl-8-(trifluoromethyl)-[1,2,4]triazolo[4,3-a]pyridin-7-amine. This compound was obtained from racemic material by SCF HPLC on a ChiralPak AS-H, 30×250 mm, 5 μm, column; using 20% IPA (w/0.1% DEA)/80% CO₂ as the mobile phase at 120 bar, 35° C., and 70 mL/min; ¹H NMR (500 MHz, METHANOL-d4) δ 8.25 (d, J=7.8 Hz, 1H), 7.08-7.00 (m, 3H), 6.97-6.88 (m, 2H), 3.57 (dd, J=14.1, 5.9 Hz, 1H), 3.38-3.28 (m, 1H), 3.18-3.11 (m, 3H), 3.01 (d, J=6.9 Hz, 2H), 1.88-1.77 (m, 1H), 1.38-1.26 (m, 1H), 1.24-1.17 (m, 1H), 1.03 (dt, J=8.6, 5.2 Hz, 1H), 0.93 (dt, J=8.9, 5.3 Hz, 1H), 0.66-0.55 (m, 2H), 0.38-0.27 (m, 2H). ee %>99%. LCMS M+1=419.18.

EXAMPLE 40

3-(Cyclopropylmethyl)-N-(((1R,2R)-2-(4-fluorophenyl)cyclopropyl)methyl)-N-methyl-8-(trifluoromethyl)-[1,2,4]triazolo[4,3-a]pyridin-7-amine. This compound was obtained from racemic material by SCF HPLC on a ChiralPak AS-H, 30×250 mm, 5 μm, column; using 20% IPA (w/0.1% DEA)/80% $CO_2$ as the mobile phase at 120 bar, 35° C., and 70 mL/min; $^1$H NMR (500 MHz, METHANOL-d4) δ 8.25 (d, J=7.8 Hz, 1H), 7.10-6.99 (m, 3H), 6.97-6.88 (m, 2H), 3.57 (dd, J=14.2, 5.8 Hz, 1H), 3.39-3.29 (m, 1H), 3.19-3.12 (m, 3H), 3.01 (d, J=6.9 Hz, 2H), 1.89-1.75 (m, 1H), 1.38-1.28 (m, 1H), 1.25-1.18 (m, 1H), 1.03 (dt, J=8.6, 5.2 Hz, 1H), 0.97-0.87 (m, 1H), 0.65-0.54 (m, 2H), 0.36-0.24 (m, 2H). ee %=97%. LCMS M+1=419.18.

EXAMPLE 41

N-(((1S,2S)-2-(4-fluorophenyl)cyclopropyl)methyl)-N-methyl-3-(2,2,2-trifluoroethyl)-8-(trifluoromethyl)-[1,2,4]triazolo[4,3-a]pyridin-7-amine. Racemic material was resolved by SCF chromatography on a ChiralPak AS-H, 30×250 mm, 5 μm, column; using 20% IPA (w/0.1% DEA)/80% $CO_2$ as the mobile phase at 120 bar, 35° C., and 70 mL/min; UV detection at 260 nm; injections were 2.0 mL (~25 mg/mL in IPA) stacked @ 20.0° intervals. $^1$H NMR (400 MHz, METHANOL-d4) δ 8.33 (d, J=7.8 Hz, 1H), 7.10 (d, J=7.8 Hz, 1H), 7.07-7.01 (m, 2H), 6.99-6.86 (m, 2H), 4.22 (q, J=10.1 Hz, 2H), 3.59 (dd, J=14.1, 5.8 Hz, 1H), 3.41-3.33 (m, 1H), 3.17 (d, J=1.3 Hz, 3H), 1.89-1.79 (m, 1H), 1.38-1.30 (m, 1H), 1.03 (dt, J=8.5, 5.3 Hz, 1H), 0.94 (dt, J=8.8, 5.4 Hz, 1H). ee %=99%. LCMS M+1=447.1.

EXAMPLE 42

N-(((1R,2R)-2-(4-fluorophenyl)cyclopropyl)methyl)-N-methyl-3-(2,2,2-trifluoroethyl)-8-(trifluoromethyl)-[1,2,4]triazolo[4,3-a]pyridin-7-amine. Racemic material was resolved by SCF chromatography on a ChiralPak AS-H, 30×250 mm, 5 μm, column; using 20% IPA (w/0.1% DEA)/80% $CO_2$ as the mobile phase at 120 bar, 35° C., and 70 mL/min; UV detection at 260 nm; injections were 2.0 mL (~25 mg/mL in IPA) stacked @ 20.0° intervals. $^1$H NMR (400 MHz, METHANOL-d4) δ 8.33 (d, J=7.8 Hz, 1H), 7.10 (d, J=8.0 Hz, 1H), 7.07-7.01 (m, 2H), 6.97-6.87 (m, 2H), 4.22 (q, J=10.3 Hz, 2H), 3.58 (dd, J=14.2, 5.9 Hz, 1H), 3.41-3.33 (m, 1H), 3.17 (d, J=1.5 Hz, 3H), 1.88-1.80 (m, 1H), 1.36-1.29 (m, 1H), 1.03 (dt, J=8.5, 5.3 Hz, 1H), 0.93 (dt, J=8.8, 5.4 Hz, 1H). ee %=98%. LCMS M+1=447.1.

EXAMPLE 43

8-Chloro-3-(cyclopropylmethyl)-N-(((1S,2S)-2-(2,5-difluorophenyl)cyclopropyl)methyl)-[1,2,4]triazolo[4,3-a]pyridin-7-amine. Racemic material was resolved by SCF chromatography on a ChiralPak AS-H, 30×250 mm, 5 μm, column; using 20% IPA (w/0.1% DEA)/80% $CO_2$ as the mobile phase at 120 bar, 35° C., and 70 mL/min; UV detection at 260 nm; injections were 2.0 mL (~25 mg/mL in IPA) stacked @ 20.0° intervals. $^1$H NMR (400 MHz, METHANOL-d4) δ 8.14 (d, J=7.5 Hz, 1H), 7.00 (td, J=9.3, 4.6 Hz, 1H), 6.92 (d, J=7.5 Hz, 1H), 6.89-6.81 (m, 1H), 6.72 (ddd, J=9.3, 6.0, 3.3 Hz, 1H), 3.57-3.40 (m, 2H), 2.97 (d, J=6.8 Hz, 2H), 2.14-2.03 (m, 1H), 1.52-1.39 (m, 1H), 1.26-1.14 (m, 1H), 1.12-1.02 (m, 1H), 0.66-0.53 (m, 2H), 0.37-0.25 (m, 2H). M+1=389.15. ee %=99.77%.

EXAMPLE 44

8-Chloro-3-(cyclopropylmethyl)-N-(((1R,2R)-2-(2,5-difluorophenyl)cyclopropyl)methyl)-[1,2,4]triazolo[4,3-a]pyridin-7-amine. Racemic material was resolved by SCF chromatography on a ChiralPak AS-H, 30×250 mm, 5 μm, column; using 20% IPA (w/0.1% DEA)/80% $CO_2$ as the mobile phase at 120 bar, 35° C., and 70 mL/min; UV detection at 260 nm; injections were 2.0 mL (~25 mg/mL in IPA) stacked @ 20.0° intervals. $^1$H NMR (400 MHz, METHANOL-d4) δ 8.13 (d, J=7.5 Hz, 1H), 6.99 (td, J=9.3, 4.5 Hz, 1H), 6.91 (d, J=7.8 Hz, 1H), 6.87-6.80 (m, 1H), 6.70 (ddd, J=9.3, 6.0, 3.0 Hz, 1H), 3.54-3.39 (m, 2H), 2.96 (d, J=7.0 Hz, 2H), 2.12-2.03 (m, 1H), 1.50-1.39 (m, 1H), 1.23-1.13 (m, 1H), 1.11-1.00 (m, 2H), 0.63-0.55 (m, 2H), 0.35-0.26 (m, 2H). M+1=389.15. ee %=97.99%.

EXAMPLE 45

8-Chloro-3-(cyclopropylmethyl)-N-(((1S,2S)-2-phenylcyclopentyl)methyl)-[1,2,4]triazolo[4,3-a]pyridin-7-amine. Racemic trans 8-chloro-3-(cyclopropylmethyl)-N-((2-phenylcyclopentyl)methyl)-[1,2,4]triazolo[4,3-a]pyridin-7-amine was resolved by chiral preparative HPLC using a Chiralcel OJ 21×250 mm, 10 micron column with a 30% ethanol/0.1% diethylamine/heptane as the mobile phase to give 8-chloro-3-(cyclopropylmethyl)-N-(((1S,2S)-2-phenylcyclopentyl)methyl)-[1,2,4]triazolo[4,3-a]pyridin-7-amine, peak 1, eluting at 6.8 min. $^1$H NMR (400 MHz, METHANOL-$d_4$) δ 8.05 (d, J=7.5 Hz, 1H), 7.33-7.20 (m, 5H), 7.20-7.08 (m, 1H), 6.60 (d, J=7.8 Hz, 1H), 3.48-3.36 (m, 1H), 2.97 (d, J=7.0 Hz, 2H), 2.83-2.66 (m, 1H), 2.40 (d, J=8.0 Hz, 1H), 2.23-2.05 (m, 2H), 1.93-1.76 (m, 3H), 1.57 (dd, J=12.7, 7.2 Hz, 1H), 1.26-1.13 (m, 1H), 0.70-0.56 (m, 2H), 0.39-0.25 (m, 2H). LCMS: M+1=381.16.

EXAMPLE 46

8-Chloro-3-(cyclopropylmethyl)-N-(((1R,2R)-2-phenylcyclopentyl)methyl)-[1,2,4]triazolo[4,3-a]pyridin-7-amine. Racemic trans 8-chloro-3-(cyclopropylmethyl)-N-((2-phenylcyclopentyl)methyl)-[1,2,4]triazolo[4,3-a]pyridin-7-amine was resolved by chiral preparative HPLC using a Chiralcel OJ 21×250 mm, 10 micron column with a 30% ethanol/0.1% diethylamine/heptane as the mobile phase to give 8-Chloro-3-(cyclopropylmethyl)-N-(((1R,2R)-2-phenylcyclopentyl)methyl)-[1,2,4]triazolo[4,3-a]pyridin-7-amine, peak 2, eluting at 9.3 min. $^1$H NMR (400 MHz, METHANOL-$d_4$) δ 8.05 (d, J=7.5 Hz, 1H), 7.33-7.20 (m, 5H), 7.20-7.08 (m, 1H), 6.60 (d, J=7.8 Hz, 1H), 3.48-3.36 (m, 1H), 2.97 (d, J=7.0 Hz, 2H), 2.83-2.66 (m, 1H), 2.40 (d, J=8.0 Hz, 1H), 2.23-2.05 (m, 2H), 1.93-1.76 (m, 3H), 1.57 (dd, J=12.7, 7.2 Hz, 1H), 1.26-1.13 (m, 1H), 0.70-0.56 (m, 2H), 0.39-0.25 (m, 2H). LCMS: M+1=381.16.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

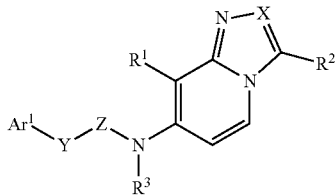

wherein:
R¹ is selected from the group consisting of cyano, halo, alkyl, haloalkyl, (cycloalkyl)alkyl, cycloalkyl, alkoxy, and haloalkoxy;
R² is selected from the group consisting of alkyl, haloalkyl, (cycloalkyl)alkyl, cycloalkyl, OR⁴, and N(R⁵)(R⁶);
R³ is hydrogen or alkyl;
R⁴ is alkyl, haloalkyl, (cycloalkyl)alkyl, or cycloalkyl;
R⁵ is alkyl, haloalkyl, (cycloalkyl)alkyl, or cycloalkyl;
R⁶ is hydrogen or alkyl;
Ar¹ is phenyl or heteroaryl and is substituted with 0-3 substituents selected from cyano, halo, alkyl, haloalkyl, cycloalkyl, alkoxy, and haloalkoxy;
X is CH or N;
Y is $C_{3-6}$ cycloalkyl substituted with 0-2 halo or alkyl substituents; and
Z is a bond or $C_{1-3}$ alkyl;
or a pharmaceutically acceptable salt thereof.

2. A compound of claim 1 where R¹ is cyano, halo, or haloalkyl; R² is alkyl, haloalkyl, or (cycloalkyl)alkyl; R³ is hydrogen or alkyl; Ar¹ is phenyl, pyridinyl, pyrimidinyl, or indanyl, and is substituted with 0-3 substituents selected from cyano, halo, alkyl, haloalkyl, cycloalkyl, alkoxy, and haloalkoxy; X is CH or N; Y is $C_{3-6}$ cycloalkyl; and Z is a bond or $C_{1-3}$ alkyl; or a pharmaceutically acceptable salt thereof.

3. A compound of claim 2 where R¹ is halo; R² is haloalkyl or (cycloalkyl)alkyl; R³ is hydrogen; Ar¹ is phenyl substituted with 0-3 halo substituents; X is N; Y is cyclopropyl; and Z is methylene; or a pharmaceutically acceptable salt thereof.

4. A compound of claim 1 where R¹ is cyano, halo, or haloalkyl.

5. A compound of claim 1 where R² is haloalkyl or (cycloalkyl)alkyl.

6. A compound of claim 1 where Ar¹ is phenyl substituted with 0-3 substituents selected from cyano, halo, alkyl, haloalkyl, cycloalkyl, alkoxy, and haloalkoxy.

7. A compound of claim 1 where Ar¹ is pyridinyl, pyridazinyl, pyrazinyl, pyrimidinyl, or indanyl, and is substituted with 0-3 substituents selected from cyano, halo, alkyl, haloalkyl, cycloalkyl, alkoxy, and haloalkoxy.

8. A compound of claim 1 where X is N.
9. A compound of claim 1 where Y is cyclopropyl.
10. A compound of claim 1 where Z is methylene.
11. A compound of claim 1 selected from the group consisting of
trans 8-chloro-3-(cyclopropylmethyl)-N-((2-(4-fluorophenyl)cyclopropyl)methyl)-[1,2,4]triazolo[4,3-a]pyridin-7-amine;
8-Chloro-3-(cyclopropylmethyl)-N-(3-phenylcyclopentyl)-[1,2,4]triazolo[4,3-a]pyridin-7-amine;
(+/−) Trans-8-chloro-3-(cyclopropylmethyl)-N-((2-phenylcyclopentyl)methyl)-[1,2,4]triazolo[4,3-a]pyridin-7-amine;
Trans-8-chloro-3-(cyclopropylmethyl)-N-((2-phenylcyclopropyl)methyl)-[1,2,4]triazolo[4,3-a]pyridin-7-amine;
8-Chloro-3-(cyclopropylmethyl)-N-(((1S,2S)-2-(4-fluorophenyl)cyclopropyl)methyl)-[1,2,4]triazolo[4,3-a]pyridin-7-amine;
Trans-8-chloro-3-(cyclopropylmethyl)-N-((2-(2-methoxyphenyl)cyclopropyl)methyl)-[1,2,4]triazolo[4,3-a]pyridin-7-amine;
Trans-8-chloro-3-(cyclopropylmethyl)-N-((2-(2-(difluoromethoxy)phenyl)cyclopropyl)methyl)-[1,2,4]triazolo[4,3-a]pyridin-7-amine;
8-Chloro-3-(cyclopropylmethyl)-N-(((1S,2S)-2-(3-methoxyphenyl)cyclopropyl)methyl)-[1,2,4]triazolo[4,3-a]pyridin-7-amine;
Trans-8-chloro-3-(cyclopropylmethyl)-N-((2-(2-(trifluoromethoxy)phenyl)cyclopropyl)methyl)-[1,2,4]triazolo[4,3-a]pyridin-7-amine;
8-Chloro-3-(cyclopropylmethyl)-N-(((1S,2S)-2-(3,6-difluoro-2-methoxyphenyl)cyclopropyl)methyl)-[1,2,4]triazolo[4,3-a]pyridin-7-amine;
8-Chloro-3-(cyclopropylmethyl)-N-(((1S,2S)-2-(2,3-dihydrobenzofuran-4-yl)cyclopropyl)methyl)-[1,2,4]triazolo[4,3-a]pyridin-7-amine;
8-Chloro-3-(cyclopropylmethyl)-N-((2-(5-fluoropyrimidin-2-yl)cyclopropyl)methyl)-[1,2,4]triazolo[4,3-a]pyridin-7-amine;
3-(Cyclopropylmethyl)-N-((2-(5-fluoropyrimidin-2-yl)cyclopropyl)methyl)-8-(trifluoromethyl)-[1,2,4]triazolo[4,3-a]pyridin-7-amine;
8-Chloro-3-(cyclopropylmethyl)-N-(1-((1R,2R)-2-(4-fluorophenyl)cyclopropyl)ethyl)-[1,2,4]triazolo[4,3-a]pyridin-7-amine;
8-Chloro-3-(cyclopropylmethyl)-N-(1-((1S,2S)-2-(4-fluorophenyl)cyclopropyl)ethyl)-[1,2,4]triazolo[4,3-a]pyridin-7-amine;
8-chloro-3-(cyclopropylmethyl)-N-((1-(4-fluorophenyl)cyclopropyl)methyl)-[1,2,4]triazolo[4,3-a]pyridin-7-amine;
2-(2-(((8-chloro-3-(cyclopropylmethyl)-[1,2,4]triazolo[4,3-a]pyridin-7-yl)amino)methyl)cyclopropyl)benzonitrile;
8-Chloro-3-(cyclopropylmethyl)-N-((2-(pyridin-4-yl)cyclopropyl)methyl)-[1,2,4]triazolo[4,3-a]pyridin-7-amine;
8-Chloro-3-(cyclopropylmethyl)-N-((2-(pyridin-3-yl)cyclopropyl)methyl)-[1,2,4]triazolo[4,3-a]pyridin-7-amine;
3-(Cyclopropylmethyl)-N-(((1S,2S)-2-(4-fluorophenyl)cyclopropyl)methyl)-8-(trifluoromethyl)-[1,2,4]triazolo[4,3-a]pyridin-7-amine;
3-(Cyclopropylmethyl)-N-(((1R,2R)-2-(4-fluorophenyl)cyclopropyl)methyl)-8-(trifluoromethyl)-[1,2,4]triazolo[4,3-a]pyridin-7-amine;
Trans-N-((2-(4-fluorophenyl)cyclopropyl)methyl)-N-methyl-3-(2,2,2-trifluoro ethyl)-8-(trifluoromethyl)-[1,2,4]triazolo[4,3-a]pyridin-7-amine;
Trans-3-(cyclopropylmethyl)-N-((2-(4-fluorophenyl)cyclopropyl)methyl)-N-methyl-8-(trifluoromethyl)-[1,2,4]triazolo[4,3-a]pyridin-7-amine;
N-((2-(4-Fluorophenyl)cyclopropyl)methyl)-3-(2,2,2-trifluoroethyl)-8-(trifluoromethyl)imidazo[1,2-a]pyridin-7-amine;
7-(((2-(3-Fluorophenyl)cyclopropyl)methyl)amino)-3-(2,2,2-trifluoroethyl)imidazo[1,2-a]pyridine-8-carbonitrile;

7-(((2-(2-Fluoro-6-methoxyphenyl)cyclopropyl)methyl) amino)-3-(2,2,2-trifluoroethyl)imidazo[1,2-a]pyridine-8-carbonitrile;

3-(2,2,2-Trifluoroethyl)-7-(((2-(2-(trifluoromethoxy)phenyl)cyclopropyl)methyl)amino)imidazo[1,2-a]pyridine-8-carbonitrile;

7-(((2-(2-Methoxyphenyl)cyclopropyl)methyl)amino)-3-(2,2,2-trifluoroethyl)imidazo[1,2-a]pyridine-8-carbonitrile;

7-(((2-(4-Fluorophenyl)cyclopropyl)methyl)amino)-3-(2,2,2-trifluoroethyl)imidazo[1,2-a]pyridine-8-carbonitrile;

N-(((1S,2S)-2-(4-Fluorophenyl)cyclopropyl)methyl)-3-(2,2,2-trifluoroethyl)-8-(trifluoromethyl)imidazo[1,2-a]pyridin-7-amine;

N-(((1R,2R)-2-(4-Fluorophenyl)cyclopropyl)methyl)-3-(2,2,2-trifluoroethyl)-8-(trifluoromethyl)imidazo[1,2-a]pyridin-7-amine;

8-Chloro-3-(cyclopropylmethyl)-N-(((1S,2S)-2-(2-fluoro-6-methoxyphenyl)cyclopropyl)methyl)-[1,2,4]triazolo[4,3-a]pyridin-7-amine;

8-Chloro-3-(cyclopropylmethyl)-N-(((1R,2R)-2-(2-fluoro-6-methoxyphenyl)cyclopropyl)methyl)-[1,2,4]triazolo[4,3-a]pyridin-7-amine;

8-Chloro-3-(cyclopropylmethyl)-N-(((1S,2S)-2-(2,3-dihydrobenzofuran-7-yl)cyclopropyl)methyl)-[1,2,4]triazolo[4,3-a]pyridin-7-amine;

8-Chloro-3-(cyclopropylmethyl)-N-(((1R,2R)-2-(2,3-dihydrobenzofuran-7-yl)cyclopropyl)methyl)-[1,2,4]triazolo[4,3-a]pyridin-7-amine;

8-Chloro-3-(cyclopropylmethyl)-N-(((1S,2S)-2-(2-fluorophenyl)cyclopropyl)methyl)-[1,2,4]triazolo[4,3-a]pyridin-7-amine;

8-Chloro-3-(cyclopropylmethyl)-N-(((1R,2R)-2-(2-fluorophenyl)cyclopropyl)methyl)-[1,2,4]triazolo[4,3-a]pyridin-7-amine;

3-(Cyclopropylmethyl)-N-(((1S,2S)-2-(4-fluorophenyl)cyclopropyl)methyl)-N-methyl-8-(trifluoromethyl)-[1,2,4]triazolo[4,3-a]pyridin-7-amine;

3-(Cyclopropylmethyl)-N-(((1R,2R)-2-(4-fluorophenyl)cyclopropyl)methyl)-N-methyl-8-(trifluoromethyl)-[1,2,4]triazolo[4,3-a]pyridin-7-amine;

N-(((1S,2S)-2-(4-fluorophenyl)cyclopropyl)methyl)-N-methyl-3-(2,2,2-trifluoroethyl)-8-(trifluoromethyl)-[1,2,4]triazolo[4,3-a]pyridin-7-amine;

N-(((1R,2R)-2-(4-fluorophenyl)cyclopropyl)methyl)-N-methyl-3-(2,2,2-trifluoroethyl)-8-(trifluoromethyl)-[1,2,4]triazolo[4,3-a]pyridin-7-amine;

8-Chloro-3-(cyclopropylmethyl)-N-(((1S,2S)-2-(2,5-difluorophenyl)cyclopropyl)methyl)-[1,2,4]triazolo[4,3-a]pyridin-7-amine;

8-Chloro-3-(cyclopropylmethyl)-N-(((1R,2R)-2-(2,5-difluorophenyl)cyclopropyl)methyl)-[1,2,4]triazolo[4,3-a]pyridin-7-amine;

8-Chloro-3-(cyclopropylmethyl)-N-(((1S,2S)-2-phenylcyclopentyl)methyl)-[1,2,4]triazolo[4,3-a]pyridin-7-amine; and 8-Chloro-3-(cyclopropylmethyl)-N-(((1R,2R)-2-phenylcyclopentyl)methyl)-[1,2,4]triazolo[4,3-a]pyridin-7-amine;

or a pharmaceutically acceptable salt thereof.

12. A composition comprising a compound of claim 1, or a pharmaceutically acceptable salt thereof, and a pharmaceutically acceptable carrier.

\* \* \* \* \*